United States Patent
Toda et al.

(10) Patent No.: US 11,040,087 B2
(45) Date of Patent: Jun. 22, 2021

(54) THERAPEUTIC AGENT FOR DISEASES ASSOCIATED WITH ABNORMALITIES IN DYSTROGLYCAN SUGAR CHAIN MODIFICATION AND METHOD FOR ASSAYING ASSOCIATED ENZYME

(71) Applicants: NATIONAL UNIVERSITY CORPORATION KOBE UNIVERSITY, Hyogo (JP); TOKYO METROPOLITAN GERIATRIC HOSPITAL AND INSTITUTE OF GERONTOLOGY, Tokyo (JP); OSAKA PREFECTURAL HOSPITAL ORGANIZATION, Osaka (JP)

(72) Inventors: Tatsushi Toda, Hyogo (JP); Kazuhiro Kobayashi, Hyogo (JP); Motoi Kanagawa, Hyogo (JP); Tamao Endo, Tokyo (JP); Hiroshi Manya, Tokyo (JP); Yoshinao Wada, Osaka (JP); Michiko Tajiri, Osaka (JP)

(73) Assignees: NATIONAL UNIVERSITY CORPORATION KOBE UNIVERSITY, Hyogo (JP); TOKYO METROPOLITAN GERIATRIC HOSPITAL AND INSTITUTE OF GERONTOLOGY, Tokyo (JP); OSAKA PREFECTURAL HOSPITAL ORGANIZATION, Osaka (JP)

( * ) Notice: Subject to any disclaimer, the term of this patent is extended or adjusted under 35 U.S.C. 154(b) by 97 days.

(21) Appl. No.: 16/324,194

(22) PCT Filed: Aug. 18, 2017

(86) PCT No.: PCT/JP2017/029600
§ 371 (c)(1),
(2) Date: Feb. 8, 2019

(87) PCT Pub. No.: WO2018/034334
PCT Pub. Date: Feb. 22, 2018

(65) Prior Publication Data
US 2020/0188491 A1 Jun. 18, 2020

(30) Foreign Application Priority Data

Aug. 18, 2016 (JP) .............................. JP2016-160390

(51) Int. Cl.
*A61K 38/45* (2006.01)
*A61P 21/00* (2006.01)
*G01N 33/68* (2006.01)

(52) U.S. Cl.
CPC .............. *A61K 38/45* (2013.01); *A61P 21/00* (2018.01); *G01N 33/6893* (2013.01)

(58) Field of Classification Search
CPC ...... A61K 38/45; A61P 21/00; G01N 33/6893
USPC ........................................................ 424/94.5
See application file for complete search history.

(56) References Cited

FOREIGN PATENT DOCUMENTS

JP 2015091229 A 5/2015

OTHER PUBLICATIONS

International Search Report issued in corresponding International Patent Application No. PCT/JP2017/029600 (with English translation of International Search Report) dated Nov. 21, 2017 (27 pages).
Endo, "Identification of CDP-ribitol and its relation with Fukuyama congenital muscular dystrophy", Bioscience & Industry, 2016, vol. 74, No. 6, pp. 513-515.
Endo, Walker-Warburg Shokogun (WWS), Bessatsu Japanese Journal of Clinical Medicine, Shin Ryoikibetsu Shokogun Series No. 32, Medical syndromes of muscular diseases (2nd edition) (first)-sonohoka no Shinkeikin Shikkan o Fukumete-, 2nd edition, 1st print, 2015, pp. 150-153.
Gerin et al., "ISPD produces CDP-ribitol used by FKTN and FKRP to transfer ribitol phosphate onto α-dystroglycan", Nature Communications, 2016, vol. 7:11534, pp. 1-15.
Kanagawa et al., "Identification of a Post-translational Modification with Ribitol-Phosphate and Its Defect in Muscular Dystrophy", Cell Reports, 2016, vol. 14, No. 9, pp. 2209-2223.
Kobayashi et al. "An ancient retrotransposal insertion causes Fukuyama-type congenital muscular dystrophy", Nature, 1998, vol. 394, pp. 388-392.

(Continued)

*Primary Examiner* — Jennifer M. H. Tichy
(74) *Attorney, Agent, or Firm* — Kilyk & Bowersox, P.L.L.C.

(57) ABSTRACT

Provided is a therapeutic agent that effectively acts on a disease associated with abnormal glycosylation of dystroglycan. Also provided is a testing method for diseases associated with abnormal glycosylation of dystroglycan. Specifically, provided is a therapeutic agent for diseases associated with abnormal glycosylation of dystroglycan, containing CDP-ribitol as an active ingredient. Ribitol-phosphate is important in the glycan structure of dystroglycan. In order for ribitol-phosphate to be incorporated into a dystroglycan glycan, a material therefor (sugar donor) is required. In the present invention, it has been found for the first time that CDP-ribitol serves as the sugar donor. It has been confirmed that the glycan of ISPD-deficient cells can be restored by administering CDP-ribitol. Thus, the present invention, which allows CDP-ribitol to be utilized for supplementation therapy, has been completed.

10 Claims, 8 Drawing Sheets
Specification includes a Sequence Listing.

(56) References Cited

OTHER PUBLICATIONS

Kobayashi et al., "Fukuyama type muscular dystrophy and related disorders : ribitol-phosphate and antisense oligonucleotid", Journal of Clinical and Experimental Medicine, 2016, vol. 259, No. 1, pp. 51-57.

Kondo-Iida et al., "Novel mutations and genotype-phenotype relationships in 107 families with Fukuyama-type congenital muscular dystrophy (FCMD)", Human Molecular Genetics, 1999, vol. 8, No. 12, pp. 2303-2309.

Kuwabara et al., "Carbohydrate-binding domain of the POMGnT1 stem region modulates O-mannosylation sites of α-dystroglycan", PNAS, 2016, vol. 113, No. 33, pp. 9280-9285.

Manya et al., "Demonstration of mammalian protein O-mannosyltransferase activity: Coexpression of POMT1 and POMT2 required for enzymatic activity", PNAS, 2004, vol. 101, No. 2, pp. 500-505.

Murakami et al., "Fukutin Gene Mutations Cause Dilated Cardiomyopathy with Minimal Muscle Weakness", American Neurological Association, 2006, vol. 60, No. 5, pp. 597-602.

Lu et al., "Mutations alter secretion of fuktin-related protein", Biochimica et Biophysica Acta, 2010, vol. 1802, pp. 253-258.

Pereira et al., "Biofunctional Catalysis by CDP-ribitol Synthase: Convergent Recruitment of Reductase and Cytidylytransferase Activities in Haemophilus influenzae and *Staphylococcus aureus*", Biochemistry, 2004, vol. 43, No. 37, pp. 11802-11812.

Praissman et al., "The functional O-mannose glycan on α-dystroglycan contains a phospho-ribitol primed for matriglycan addition", eLIFE, 2016, vol. 5, pp. 1-28.

Riemersma et al., Human ISPD Is a Cytidyltransferase Required for Dystroglycan O-Mannosylation, Chemistry & Biology, 2015, vol. 22, pp. 1643-1652.

Toda et al., "Discovery of new cause of muscular dystrophy cause expected treatment development", Cell Reports, 2016, http://www.kobe-u.ac.jp/NEWS/research/2016_02_26_01.html.

Toda, "Recent development of therapy for muscular dystrophy", Division of Neurology/Molecular Brain Science, Kobe University Graduate School of Medicine, 2015, vol. 5, pp. 135-145.

Yoshida et al., "Muscular Dystrophy and Neuronal Migration Disorder Caused by Mutations in a Glycosyltransferase, POMGnT1", Developmental Cell, 2001, vol. 1, pp. 717-724.

THERAPEUTIC AGENT FOR DISEASES ASSOCIATED WITH ABNORMALITIES IN DYSTROGLYCAN SUGAR CHAIN MODIFICATION AND METHOD FOR ASSAYING ASSOCIATED ENZYME

The present application is a National Stage Application of PCT/JP2017/029600, filed Aug. 18, 2017, which claims priority from Japanese Patent Application No. 2016-160390, which is incorporated herein by reference.

TECHNICAL FIELD

The present invention relates to a therapeutic agent for diseases associated with abnormal glycosylation of dystroglycan, containing cytidine diphosphate ribitol (CDP-ribitol: CDP-Rbo) as an active ingredient.

The present application claims priority from Japanese Patent Application No. 2016-160390, which is incorporated herein by reference.

BACKGROUND ART

Muscular dystrophy is a genetic muscular disease involving necrosis/regeneration of skeletal muscles as a major lesion, and 50 or more causative genes therefor have been elucidated. Muscular dystrophy involves motor dysfunction associated with skeletal muscle disorder as a cardinal symptom, and is often complicated with various symptoms, such as joint contracture/deformation, respiratory dysfunction, myocardial disorder, and swallowing dysfunction. While reduced motor function is the cardinal symptom, there are variations in onset timing, clinical features, and rate of progression depending on disease types. Typical disease types include Fukuyama congenital muscular dystrophy (FCMD), dystrophinopathy (Duchenne/Becker muscular dystrophy), limb-girdle muscular dystrophy, facioscapulohumeral muscular dystrophy, Emery-Dreifuss muscular dystrophy, oculopharyngeal muscular dystrophy, myotonic dystrophy, and the like. None of the disease types has a radical therapy. Only symptomatic treatments, such as a limited effect of a corticosteroid on Duchenne muscular dystrophy, functional maintenance through rehabilitation, assisted ventilation care, and a cardiac pacemaker, are available.

Of the muscular dystrophies, FCMD is known to be due to an abnormality in a fukutin (FKTN) gene. In addition to FCMD, various pathological conditions are caused in association with a mutation in the fukutin gene. Examples thereof include adult-onset dilated cardiomyopathy (Non Patent Literature 1) and Walker-Warburg syndrome (WWS)-like severe congenital muscular dystrophy (Non Patent Literature 2). For treatment of a disease caused by an SVA retrotransposon insertion mutation in the fukutin gene, there is a report on an antisense nucleic acid capable of expressing normal fukutin mRNA at a transcription stage of the insertion mutant fukutin gene to restore production of a normal fukutin protein (Patent Literature 1).

Dystroglycan (DG) was discovered as a component of a dystrophin-glycoprotein complex (DGC) from skeletal muscles. Dystroglycan is a cell surface receptor for an extracellular matrix molecule or synaptic molecule, and plays an important role in various tissues. Dystroglycan is subjected to post-translational modification by a unique mechanism to acquire ligand-binding activity. It is said that abnormal glycosylation of dystroglycan causes muscular dystrophy accompanied by brain malformation or mental retardation.

DGC is a molecular complex formed of dystrophin and membrane-associated glycoproteins. DGC forms a structure connecting a basement membrane and an actin skeleton. It is considered that the DGC-mediated basement membrane-cytoskeleton linking is important for maintaining such a strength of a muscle cell membrane as to be capable of withstanding a mechanical stress such as expansion and contraction of muscles. Dystroglycan secures dystrophin directly beneath the cell membrane, and at the same time, is extracellularly bound to a basement membrane molecule, such as laminin, to function as a molecular axis connecting the cytoskeleton and the basement membrane. Dystroglycan is formed of α and β subunits, both of which are encoded in a single mRNA, and is cleaved into α-dystroglycan (α-DG) and β-dystroglycan β-DG) in a process of post-translational modification. α-DG is subjected to a high degree of glycosylation, and serves a function of binding to a ligand as an extracellular subunit.

It was confirmed in the late 1990s that the glycan of dystroglycan contains a glycan structure such as sialic acid (Sia)-galactose (Gal)-N-acetylglucosamine (GlcNAc)-mannose (Man), and the glycan extends from serine or threonine of dystroglycan. It has been reported that causative genes (POMGNT1 and POMT) for muscle-eye-brain disease (MEB) and WWS, which are FCMD type related diseases, are glycosyltransferases that link GlcNAc and Man (Non Patent Literatures 3 and 4). However, actions of causative genes for glycan abnormality-type muscular dystrophy, such as fukutin, fukutin-related protein (FKRP), and isoprenoid synthase domain-containing protein (ISPD), have been unknown.

There is a report predicting that ISPD has cytidine transferase activity on the basis of the fact that a structure of a bacterial enzyme for biosynthesizing CDP-ribitol (CDP-Rbo) is similar to a crystal structure of ISPD (Non Patent Literature 5). In Non Patent Literature 5, it is suggested that the cytidine transferase activity allows CDP-ribulose, CDP-ribose, and CDP-ribitol to be synthesized from cytidine triphosphate (CTP). However, it is not demonstrated at all what substance or synthesis reaction acts physiologically, and it is only predicted that ISPD has cytidine transferase activity. In addition, in Non Patent Literature 5, there is no disclosure or suggestion of the dystroglycan glycan.

CITATION LIST

Non Patent Literature

[NPL 1] Ann. Neurol., 60, 597-602 (2006)
[NPL 2] Hum. Mol., Genet., 8, 2303-2309 (1999)
[NPL 3] Dev Cell., 1(5), 717-24 (2001)
[NPL 4] Proc Natl Acad Sci USA., 101(2), 500-5 (2004)
[NPL 5] Chemistry & Biology, 22(12), 1643-52 (2015)

Patent Literature

[PTL 1] JP 2015-91229 A

SUMMARY OF INVENTION

Technical Problem

It is an object of the present invention to provide a therapeutic agent that effectively acts on a disease associated with abnormal glycosylation of dystroglycan. It is another object of the present invention to provide a testing method for diseases associated with abnormal glycosylation of dystroglycan.

Solution to Problem

The inventors of the present invention have made detailed analysis of the glycan structure of dystroglycan, and as a result, have found for the first time that ribitol-phosphate is present in the glycan structure. Hitherto, ribitol-phosphate has not been found in mammals, and has been found only in bacteria and some plants. In order for ribitol-phosphate to be incorporated into a dystroglycan glycan, a material therefor (sugar donor) is required. In view of this, the inventors have confirmed that CDP-ribitol serves as the sugar donor, and in the present invention, have found for the first time that ISPD has CDP-ribitol synthase activity in mammals. In addition, in the present invention, the inventors have also confirmed for the first time that fukutin and FKRP are each a transferase for incorporating ribitol-phosphate into the glycan of dystroglycan through the use of CDP-ribitol as the sugar donor. Further, the inventors have confirmed that the dystroglycan glycan can be restored by administering CDP-ribitol to ISPD-deficient cells. Thus, the inventors have completed the present invention, which allows CDP-ribitol to be utilized for supplementation therapy.

That is, the present invention includes the following.

1. A therapeutic agent for diseases associated with abnormal glycosylation of dystroglycan, including CDP-ribitol as an active ingredient.
2. The therapeutic agent according to Item 1, wherein the disease associated with abnormal glycosylation of dystroglycan includes a disease that occurs in association with an abnormality in any one gene selected from ISPD, FKRP, fukutin, POMT1, POMT2, DAG1, LARGE, DPM1, DPM2, DPM3, B3GALNT2, GMPPB, TMEM5, POMK, DOLK, POMGNT1, POMGNT2, and B4GAT1.
3. The therapeutic agent according to Item 1 or 2, wherein the abnormal glycosylation of dystroglycan includes an abnormality in ribitol-phosphate in a dystroglycan glycan.
4. The therapeutic agent according to any one of Items 1 to 3, wherein the disease associated with abnormal glycosylation of dystroglycan includes α-dystroglycanopathy.
5. The therapeutic agent according to Item 4, wherein the α-dystroglycanopathy includes any one selected from Fukuyama muscular dystrophy, Walker-Warburg syndrome, muscle-eye-brain disease (MEB), limb-girdle muscular dystrophy type 2I, limb-girdle muscular dystrophy type 2M, and cardiomyopathy.
6. The therapeutic agent according to Item 2, wherein the disease associated with abnormal glycosylation of dystroglycan includes a disease that causes an abnormality in biosynthesis of a laminin-binding glycan in association with an abnormality in an ISPD gene.
7. A testing method for muscular dystrophy, including detecting an abnormality in ribitol-phosphate in a dystroglycan glycan.
8. An assay method for fukutin activity, including the following steps:
    1) a step of performing a reaction by adding a specimen to a system including GalNAcβ1-3GlcNAc as a substrate and CDP-ribitol as a sugar donor; and
    2) a step of assaying GalNAcβ1-3GlcNAc containing one molecule of ribitol-phosphate serving as a reaction product.
9. An assay method for fukutin activity, including the following steps:
    1) a step of performing a reaction by adding a specimen to a system including a phosphorylated Core M3-modified peptide as a substrate and CDP-ribitol as a sugar donor; and
    2) a step of assaying a phosphorylated Core M3-modified peptide containing one molecule of ribitol-phosphate serving as a reaction product.
10. The assay method for fukutin activity according to Item 9, wherein the phosphorylated Core M3-modified peptide includes a phosphorylated Core M3-modified peptide including (SEQ ID NO: 2)
Ac-AT(Man)PAPVAAIGPK-NH$_2$.

11. An assay method for FKRP activity, including the following steps:
    1) a step of performing a reaction by adding a specimen to a system including GalNAcβ1-3GlcNAc having added thereto one molecule of ribitol-phosphate as a substrate and CDP-ribitol as a sugar donor; and
    2) a step of assaying GalNAcβ1-3GlcNAc containing two molecules of ribitol-phosphate serving as a reaction product.
12. An assay method for FKRP activity, including the following steps:
    1) a step of performing a reaction by adding a specimen to a system including a phosphorylated Core M3-modified peptide having added thereto one molecule of ribitol-phosphate as a substrate and CDP-ribitol as a sugar donor; and
    2) a step of assaying a phosphorylated Core M3-modified peptide containing two molecules of ribitol-phosphate serving as a reaction product.
13. The assay method for FKRP activity according to Item 12, wherein the phosphorylated Core M3-modified peptide includes a phosphorylated Core M3-modified peptide including (SEQ ID NO: 2)
Ac-AT(Man)PAPVAAIGPK-NH$_2$.

14. A method of analyzing an ameliorating effect on a glycan abnormality, including:
    adding CDP-ribitol or a mixture thereof with a nucleic acid transfection reagent to cells deficient or mutated in a gene for any one of ISPD, fukutin, and FKRP;
    culturing the cells;
    collecting the cells; and
    analyzing a dystroglycan glycan.
15. A reagent, including secretion-type fukutin.
16. A reagent, including secretion-type FKRP.
17. A kit for fukutin activity assay, including, as components, a reagent containing GalNAcβ1-3GlcNAcβ1 and a reagent containing CDP-ribitol, or a kit for fukutin activity assay, including the components and a reagent containing secretion-type fukutin as another component.
18. A kit for fukutin activity assay, including, as components, a reagent containing a phosphorylated Core M3-modified peptide and a reagent containing CDP-ribitol, or a kit for fukutin activity assay, including the components and a reagent containing secretion-type fukutin as another component.
19. A kit for FKRP activity assay, including, as components, a reagent containing GalNAcβ1-3GlcNAcβ1 having added thereto one molecule of ribitol-phosphate and a reagent containing CDP-ribitol, or a kit for FKRP activity assay, including the components and a reagent containing secretion-type FKRP as another component.

20. A kit for FKRP activity assay, including, as components, a reagent containing a phosphorylated Core M3-modified peptide having added thereto one molecule of ribitol-phosphate and a reagent containing CDP-ribitol, or a kit for FKRP activity assay, including the components and a reagent containing secretion-type FKRP as another component.

Advantageous Effects of Invention

The therapeutic agent for diseases associated with abnormal glycosylation of dystroglycan, containing CDP-ribitol as an active ingredient, of the present invention can restore the dystroglycan glycan, and effectively acts on the treatment of the disease and/or the amelioration of symptoms associated with the disease.

In the case of a patient with a mutation in fukutin or FKRP, it is considered that the enzymatic activity of fukutin or FKRP does not become zero owing to the mutation, and a little activity remains. When the activity of fukutin or FKRP becomes zero, the patient cannot survive, and hence is not born. In such case, when CDP-ribitol serving as a material for the enzymatic reaction of fukutin or FKRP is present in a large amount, the transfer and incorporation of ribitol-phosphate into the dystroglycan glycan is considered to proceed through the utilization of the remaining enzymatic activity. That is, CDP-ribitol supplementation therapy can be expected to exhibit an effect on not only an ISPD mutant, but also a fukutin or FKRP mutant. In addition, even in the case of a gene other than ISPD, fukutin, and FKRP, as long as the gene influences ribitol-phosphate in glycosylation of dystroglycan, the therapeutic agent containing CDP-ribitol as an active ingredient of the present invention can effectively act also on a disease associated with abnormal glycosylation of dystroglycan caused by an abnormality in such gene.

BRIEF DESCRIPTION OF DRAWINGS

FIG. 2 is also a diagram for illustrating the functions of ISPD, fukutin, and FKRP given as responsible genes for diseases associated with abnormal glycosylation of dystroglycan.

DESCRIPTION OF EMBODIMENTS

The present invention relates to a therapeutic agent that effectively acts on a disease associated with abnormal glycosylation of dystroglycan. As such therapeutic agent, CDP-ribitol is contained as an active ingredient.

As used herein, the term "abnormal glycosylation of dystroglycan" refers to a quantitative abnormality as well as a structural abnormality in a dystroglycan glycan. As sugars serving as constituent components of a dystroglycan glycan, there are given, for example, glucuronic acid, xylose, ribitol-phosphate, galactosamine, glucosamine, and mannose phosphate. In particular, ribitol-phosphate is important. In order for ribitol-phosphate to be incorporated into the dystroglycan glycan, a material therefor (sugar donor) is required. In the present invention, it has been confirmed for the first time that CDP-ribitol serves as the sugar donor, and that ISPD is a mammalian CDP-ribitol synthase (see FIG. 2). Further, in the present invention, it has also been confirmed for the first time that fukutin and FKRP are each a transferase that transfers ribitol 5-phosphate to the sugar (to the GalNAc-3 position, or the C1 position of ribitol 5-phosphate, respectively) through the use of CDP-ribitol as the sugar donor (see FIG. 2).

Figure 1:
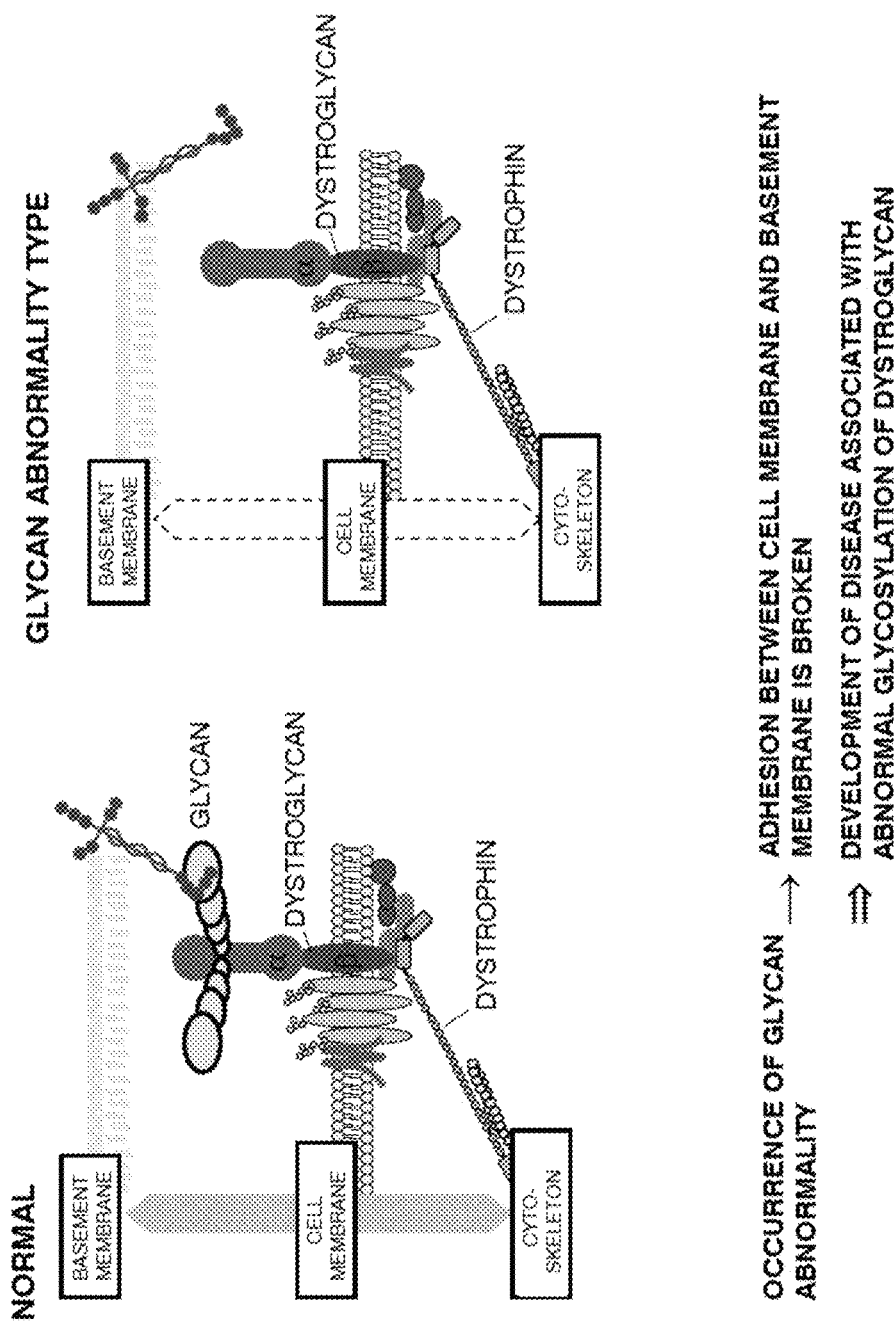
FIG. 1 is a diagram for schematically illustrating a mode of abnormal glycosylation of dystroglycan.

As used herein, the term "disease associated with abnormal glycosylation of dystroglycan" refers to, for example, a disease associated with a structural and/or quantitative abnormality in a dystroglycan glycan. Of the α-dystroglycan (α-DG) and β-dystroglycan (β-DG) subunits constituting dystroglycan, α-DG is subjected to a high degree of glycosylation. α-DG plays a role in binding to a ligand, such as laminin, neurexin, or agrin, as an extracellular subunit to connect the basement membrane and the cytoskeleton (see FIG. 1). In association with abnormal glycosylation of α-DG, the ligand-binding ability of dystroglycan is lost or weakened, and thus adhesion between the cell membrane and the basement membrane is broken, resulting in a disease. Examples of such disease include so-called α-dystroglycanopathy, dilated cardiomyopathy, and a tumor associated with abnormal glycosylation of α-DG. Examples of the so-called α-dystroglycanopathy include diseases given as examples in The Journal of Biochemistry, Vol. 86, No. 4, 452-463 (2014), specifically muscular dystrophies (dystroglycanopathies), more specifically FCMD, WWS, MEB disease, limb-girdle muscular dystrophy type 2I, and limb-girdle muscular dystrophy type 2M. The tumor is, for example, any one of the tumors listed in Molecular Cancer (2015) 14: 141, Proc Natl Acad Sci USA. 2009 Jul. 21; 106 (29): 12109-14, Cancer Res. 2004 Sep. 1; 64 (17): 6152-9, and the like.

As responsible genes for the disease associated with abnormal glycosylation of dystroglycan of the present invention, there are given, for example, ISPD, FKRP, fukutin, POMT1, POMT2, DAG1, LARGE, DPM1, DPM2, DPM3, B3GALNT2, GMPPB, TMEM5, POMK, DOLK, POMGNT1, POMGNT2, and B4GAT1. Preferred examples thereof include ISPD, FKRP, and fukutin. The disease associated with abnormal glycosylation of dystroglycan of the present invention also encompasses a disease that occurs in association with an abnormality caused by, for example, the deletion of any one gene selected from the genes listed above, a mutation therein, or reduced expression thereof due to an epigenetic change. As the disease associated with abnormal glycosylation of dystroglycan, there has been reported, for example, renal cancer. In those diseases and the like, abnormalities in LARGE2 and ISPD have been observed (Miller et al. Molecular Cancer (2015) 14: 141). In addition, muscle weakness or the like due to dilated cardiomyopathy caused by an abnormality in the fukutin gene has also been reported (Non Patent Literature 1). Any disease other than the diseases specifically shown above is also encompassed as the target disease of the present invention as long as the disease occurs in association with an abnormality in any of the genes listed above. In particular, the disease is a disease that causes an abnormality in biosynthesis of a laminin-binding glycan in association with an abnormality in the ISPD gene. In addition, the therapeutic agent containing CDP-ribitol as an active ingredient of the present invention can effectively act in the case of not only an ISPD mutant, but also a fukutin or FKRP mutant, or a mutation in a gene that influences ribitol-phosphate in glycosylation of dystroglycan.

The therapeutic agent of the present invention contains CDP-ribitol as an active ingredient. Herein, the CDP-ribitol to be contained as the active ingredient may be a compound having a structure represented by the following formula (I), a derivative of the compound, or a pharmaceutically acceptable salt or hydrate of the compound or the derivative of the compound.

[Chemical I]

Formula (I)

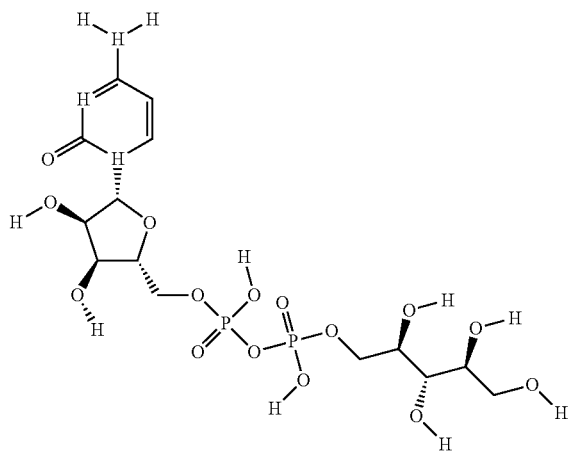

The therapeutic agent of the present invention contains CDP-ribitol as an active ingredient, and may be formulated by appropriately blending a pharmaceutically acceptable carrier or additive. The blending ratio of the carrier or the additive only needs to be appropriately set on the basis of a range that is generally adopted in the field of pharmaceuticals. The carrier or the additive that may be blended is not particularly limited, and examples thereof include: various carriers, such as water, physiological saline, other aqueous solvents, and an aqueous or oily base; and various non-toxic additives, such as an excipient, a binder, a pH adjusting agent, a disintegrant, an absorption promoter, a lubricant, a colorant, a flavoring substance, a perfume, an antiseptic, a tonicity agent, a stabilizer, a dispersant, an antioxidant, and a buffer. Examples of the non-toxic additive include starch, gelatin, glucose, lactose, fructose, maltose, magnesium carbonate, talc, magnesium stearate, methyl cellulose, carboxymethyl cellulose, gum arabic, polyethylene glycol, propylene glycol, petrolatum, glycerin, ethanol, syrup, sodium chloride, sodium sulfite, sodium phosphate, citric acid, and polyvinylpyrrolidone.

The therapeutic agent of the present invention may be used by being administered to a patient with the "disease associated with abnormal glycosylation of dystroglycan" described above to treat the disease and/or alleviate symptoms associated with the disease. An administration route is not particularly limited, but may be oral administration or parenteral administration.

The therapeutic agent of the present invention only needs to be formulated into a dosage form suitable for each administration method. As a formulation form for the oral administration, there are given, for example, a tablet, a capsule, a granule, a powder, a fine granule, a pill, a troche, a sublingual tablet, a suppository, an ointment, an emulsion, a suspension, and a syrup. For the parenteral administration, there are given an injection and a transdermal formulation. The injection may be, for example, intravenously administered, subcutaneously administered, or intramuscularly administered, and the transdermal formulation may be locally administered by, for example, transdermal administration or transmucosal administration. Another drug may be incorporated into the formulation in order to reinforce or enhance the usefulness of the present invention.

The dose of the therapeutic agent of the present invention varies depending on the severity of the target disease, a therapeutic purpose, and the like, and also varies depending on the dosage form, the administration route, and the age and body weight of the patient. For example, when administered as an injection, the therapeutic agent may be administered at from about 0.01 mg to about 60 g, preferably from about 0.1 mg to about 24 g, more preferably from about 0.1 mg to about 6 g per day. An administration interval may be set to an interval of from 1 time to several times per day, or from 1 day to 2 weeks.

The therapeutic agent of the present invention may be used for a patient with the "disease associated with abnormal glycosylation of dystroglycan" described above simultaneously with, or before or after a drug that acts by a different action mechanism, such as an antisense nucleic acid disclosed in Patent Literature 1 (JP 2015-91229 A) (antisense nucleic acid containing a sequence complementary to the base sequence of pre-mRNA for an insertion mutant fukutin gene, for treatment).

The present invention also encompasses a testing method for muscular dystrophy, including detecting an abnormality in ribitol-phosphate in a dystroglycan glycan. Examples of the muscular dystrophy include FCMD, dystrophinopathy (Duchenne/Becker muscular dystrophy), limb-girdle muscular dystrophy, facioscapulohumeral muscular dystrophy, Emery-Dreifuss muscular dystrophy, oculopharyngeal CDP-ribitol type muscular dystrophy, and myotonic dystrophy. Some muscular dystrophies are due to causes different from the abnormal glycosylation of dystroglycan. When the disease type of the muscular dystrophy is determined through the detection of an abnormality in ribitol-phosphate in the dystroglycan glycan in a patient with muscular dystrophy, a more appropriate therapeutic method can be selected.

Further, the present invention also encompasses an assay method for fukutin activity or FKRP activity. In the present invention, the activity of each of fukutin and FKRP has been confirmed, and as a result, it is considered that fukutin and FKRP each have ribitol transferase activity, and specifically, are each a transferase that binds Rbo5P into a glycan using Rbo5P from CDP-ribitol to synthesize a glycan. Fukutin has enzymatic activity shown in FIG. 5, and FKRP has enzymatic activity shown in FIG. 6. On the basis of such enzymatic reaction, ribitol transferase activity in a specimen may be assayed. Further, in the present invention, through the use of the assay method for fukutin activity or FKRP activity, a compound that influences the activity of fukutin or FKRP may be selected by screening from a plurality of candidate compounds. The compound that influences the activity of fukutin or FKRP may be a low-molecular-weight compound, or may be, for example, a protein or a high-molecular-weight compound constituting part thereof.

The enzymatic activity of fukutin may be assayed by, for example, a method including the following steps 1) and 2). Core M3 is part of the glycans constituting the dystroglycan glycan, and contains GalNAcβ1-3GlcNAc as a glycan.

1) A step of performing a reaction by adding a specimen to a system including GalNAcβ1-3GlcNAc as a substrate and CDP-ribitol as a sugar donor; and 2) a step of assaying GalNAcβ1-3GlcNAc containing one molecule of ribitol-phosphate serving as a reaction product.

1) A step of performing a reaction by adding a specimen to a system including a phosphorylated Core M3-modified peptide as a substrate and CDP-ribitol as a sugar donor; and 2) a step of assaying a phosphorylated Core M3-modified peptide containing one molecule of ribitol-phosphate serving as a reaction product.

An example of the peptide sequence of the phosphorylated Core M3-modified peptide in the step 1) is Ac-AT(Man)PAPVAAIGPK-NH$_2$ (SEQ ID NO: 2).

Through the utilization of the assay method for fukutin activity, a compound that influences the activity of fukutin may be selected by allowing fukutin and a candidate compound to act. This may be performed by, for example, a method including the following steps 1') and 2').

1') A step of performing a reaction by adding secretion-type fukutin and a candidate compound to a system including GalNAcβ1-3GlcNAc as a substrate and CDP-ribitol as a sugar donor; and 2') a step of assaying GalNAcβ1-3GlcNAc containing one molecule of ribitol-phosphate serving as a reaction product.

1') A step of performing a reaction by adding secretion-type fukutin and a candidate compound to a system including a phosphorylated Core M3-modified peptide as a substrate and CDP-ribitol as a sugar donor; and 2) a step of assaying a phosphorylated Core M3-modified peptide containing one molecule of ribitol-phosphate serving as a reaction product.

An example of the peptide sequence of the phosphorylated Core M3-modified peptide in the step 1') is Ac-AT(Man) PAPVAAIGPK-NH$_2$ (SEQ ID NO: 2). In the above-mentioned steps 1') and 2'), a system including no candidate compound in the step 1') may be assayed as a control. When the candidate compound has an action of enhancing the activity of fukutin, the reaction product shows a higher value than the control, and when the candidate compound has an action of reducing the activity of fukutin, the reaction product shows a lower value than the control.

For example, gene information on human fukutin is disclosed in GenBank RefSeq: NM_006731 (SEQ ID NO: 3), and its amino acid sequence is identified by the following SEQ ID NO: 4. Secretion-type fukutin is fukutin without a transmembrane domain, and is also extracellular secretion-type fukutin. Secretion-type fukutin may be generated by being expressed as a secretion-type recombinant obtained by removing the transmembrane domain of fukutin. Secretion-type fukutin has, for example, a structure containing the sequence from Tyr28 to the stop codon in the amino acid sequence set forth in SEQ ID NO: 4. To its N-terminus, an amino acid sequence set forth in SEQ ID NO: 5 may be added. The sequence set forth in SEQ ID NO: 5 is the signal sequence of *Gaussia* luciferase, His/myc tags, restriction enzyme site.

```
Amino Acid Sequence of Human Fukutin
                                  (SEQ ID NO: 4)
MSRINKNVVLALLTLTSSAFLLFQLYYYKHYLSTKNGAGLSKSKGSRIGF

DSTQWRAVKKFIMLTSNQNVPVFLIDPLILELINKNFEQVKNTSHGSTSQ

CKFFCVPRDFTAFALQYHLWKNEEGWFRIAENMGFQCLKIESKDPRLDGI

DSLSGTEIPLHYICKLATHAIHLVVFHERSGNYLWHGHLRLKEHIDRKFV

PFRKLQFGRYPGAFDRPELQQVTVDGLEVLIPKDPMHFVEEVPHSRFIEC

RYKEARAFFQQYLDDNTVEAVAFRKSAKELLQLAAKTLNKLGVPFWLSSG

TCLGWYRQCNIIPYSKDVDLGIFIQDYKSDIILAFQDAGLPLKHKFGKVE

DSLELSFQGKDDVKLDVFFFYEETDHMWNGGTQAKTGKKFKYLFPKFTLC

WTEFVDMKVHVPCETLEYIEANYGKTWKIPVKTWDWKRSPPNVQPNGIWP

ISEWDEVIQLY

Additional Sequence
                                  (SEQ ID NO: 5)
MGVKVLFALICIAVAEAKPTHHHHHHEQKLISEEDLRNS
```

The enzymatic activity of FKRP may be assayed by, for example, a method including the following steps 1) and 2) as with the enzymatic activity of fukutin described above.

1) A step of performing a reaction by adding a specimen to a system including GalNAcβ1-3GlcNAc having added thereto one molecule of ribitol-phosphate as a substrate and CDP-ribitol as a sugar donor; and 2) a step of assaying GalNAcβ1-3GlcNAc containing two molecules of ribitol-phosphate serving as a reaction product.

1) A step of performing a reaction by adding a specimen to a system including a phosphorylated Core M3-modified peptide having added thereto one molecule of ribitol-phosphate as a substrate and CDP-ribitol as a sugar donor; and 2) a step of assaying a phosphorylated Core M3-modified peptide containing two molecules of ribitol-phosphate serving as a reaction product.

An example of the peptide sequence of the phosphorylated Core M3-modified peptide in the step 1) is Ac-AT(Man)PAPVAAIGPK-NH$_2$ (SEQ ID NO: 2).

Through the utilization of the assay method for FKRP activity, a compound that influences the activity of FKRP may be selected by allowing FKRP and a candidate compound to act. This may be performed by, for example, a method including the following steps 1') and 2').

1') A step of performing a reaction by adding secretion-type FKRP and a candidate compound to a system including GalNAcβ1-3GlcNAc having added thereto one molecule of ribitol-phosphate as a substrate, and CDP-ribitol as a sugar donor; and 2) a step of assaying GalNAcβ1-3GlcNAc containing two molecules of ribitol-phosphate serving as a reaction product.

1') A step of performing a reaction by adding secretion-type FKRP and a candidate compound to a system including a phosphorylated Core M3-modified peptide having added thereto one molecule of ribitol-phosphate as a substrate, and CDP-ribitol as a sugar donor; and 2) a step of assaying a phosphorylated Core M3-modified peptide containing two molecules of ribitol-phosphate serving as a reaction product.

An example of the peptide sequence of the phosphorylated Core M3-modified peptide in the step 1') is Ac-AT (Man) PAPVAAIGPK-NH$_2$ (SEQ ID NO: 2). In the above-mentioned steps 1') and 2'), a system including no candidate compound in the step 1') is assayed as a control. When the candidate compound has an action of enhancing the activity of FKRP, the reaction product shows a higher value than the control, and when the candidate compound has an action of reducing the activity of FKRP, the reaction product shows a lower value than the control.

For example, gene information on human FKRP is disclosed in GenBank RefSeq: NM_024301 (SEQ ID NO: 6), and its amino acid sequence is identified by the following SEQ ID NO: 7. Secretion-type FKRP is FKRP without a transmembrane domain, and is also extracellular secretion-type FKRP. Secretion-type FKRP may be generated by being expressed as a secretion-type recombinant obtained by removing the transmembrane domain of FKRP. Secretion-type FKRP has, for example, a structure containing the sequence from Asn33 to the stop codon in the amino acid sequence set forth in SEQ ID NO: 7. To its N-terminus, an amino acid sequence set forth in SEQ ID NO: 8 may be added. The sequence set forth in SEQ ID NO: 8 is the signal sequence of murine preprotrypsin, His/myc tags.

Amino Acid Sequence of Human FKRP (SEQ ID NO: 7)

MRLTRCQAALAAAITLNLLVLFYVSWLQHQPRNSRARGPRRASAAGPRVT

VLVREFEAFDNAVPELVDSFLQQDPAQPVVVAADTLPYPPLALPRIPNVR

LALLQPALDRPAAASRPETYVATEFVALVPDGARAEAPGLLERMVEALRA

GSARLVAAPVATANPARCLALNVSLREWTARYGAAPAAPRCDALDGDAVV

LLRARDLFNLSAPLARPVGTSLFLQTALRGWAVQLLDLTFAAARQPPLAT

AHARWKAEREGRARRAALLRALGIRLVSWEGGRLEWFGCNKETTRCFGTV

VGDTPAYLYEERWTPPCCLRALRETARYVVGVLEAAGVRYWLEGGSLLGA

ARHGDIIPWDYDVDLGIYLEDVGNCEQLRGAEAGSVVDERGFVWEKAVEG

DFFRVQYSESNHLHVDLWPFYPRNGVMTKDTWLDHRQDVEFPEHFLQPLV

PLPFAGFVAQAPNNYRRFLELKFGPGVIENPQYPNPALLSLTGSG

Additional Sequence (SEQ ID NO: 8)

MSALLILALVGAAVADYKHHHHHHEQKLISEEDLR

The enzymatic reaction of fukutin or FKRP is achieved by, for example, performing the reaction under the temperature condition of 37±1° C. for from 5 minutes to 48 hours, preferably from 1 hour to 24 hours. Fukutin specifically has enzymatic activity shown in FIG. 5, and the reaction product is, for example, a phosphorylated Core M3-modified peptide containing one molecule of ribitol-phosphate. It is considered that fukutin is a transferase that binds Rbo5P from CDP-ribitol to, for example, a GalNAc-3 position in a glycan to synthesize a glycan (CDP-Rbo: GalNAc-3 Rbo5P transferase). FKRP specifically has enzymatic activity shown in FIG. 6, and the reaction product is, for example, a phosphorylated Core M3-modified peptide containing two molecules of ribitol-phosphate. It is considered that FKRP is a transferase that binds Rbo5P from CDP-ribitol to, for example, the C1 position of ribitol 5-phosphate in a glycan to synthesize a glycan (CDP-Rbo: Rbo5P-1 Rbo5P transferase).

The reaction product obtained by the enzymatic reaction of fukutin or FKRP, such as the phosphorylated Core M3 containing one molecule of ribitol-phosphate or the phosphorylated Core M3-modified peptide containing two molecules of ribitol-phosphate, may be assayed by a method known per se, such as HPLC, mass spectrometry, LC/MS, or radioisotope-labeled CDP-ribitol, or any method to be developed in the future.

The present invention also encompasses the secretion-type fukutin or secretion-type FKRP described above. A reagent containing secretion-type fukutin (hereinafter referred to as "secretion-type fukutin reagent") or a reagent containing secretion-type FKRP (hereinafter referred to as "secretion-type FKRP reagent") may be effectively used in an assay system for the enzymatic reaction of fukutin or FKRP, and may be used for, for example, screening of compounds. The secretion-type fukutin reagent or secretion-type FKRP reagent that may be used for such assay system may also be used as a respective authentic enzyme sample for assay.

The present invention further encompasses a kit for fukutin activity assay and a kit for FKRP assay. Each of those kits for activity assay includes at least a reagent for a substrate as a component, and may include, as a component, a reagent containing a sugar donor and/or a reagent containing an enzyme source.

The kit for fukutin activity assay may include the following as components. As the reagent for a substrate, any one of a reagent containing GalNAcβ1-3GlcNAc (hereinafter referred to as "GalNAcβ1-3GlcNAc reagent") or a reagent containing a phosphorylated Core M3-modified peptide (hereinafter referred to as "phosphorylated Core M3-modified peptide reagent") may be selected. An example of the peptide sequence of the phosphorylated Core M3-modified peptide is Ac-AT (Man) PAPVAAIGPK-NH$_2$ (SEQ ID NO: 2). An example of the reagent containing a sugar donor is a reagent containing CDP-ribitol (hereinafter referred to as "CDP-ribitol reagent"). As the reagent containing an enzyme source, a reagent containing secretion-type fukutin (hereinafter referred to as "secretion-type fukutin reagent") may be used. For example, when only fukutin activity in a specimen is to be assayed, the secretion-type fukutin reagent may not be used. In addition, in, for example, the case of confirming the activity of a compound that influences the activity of fukutin, the secretion-type fukutin reagent may be used. The secretion-type fukutin reagent may also be used as an authentic enzyme sample for fukutin.

The kit for FKRP activity assay may include the following as components. As the reagent for a substrate, any one of a reagent containing GalNAcβ1-3GlcNAc having added thereto one molecule of ribitol-phosphate (hereinafter referred to as "ribitol-phosphate 1 GalNAcβ1-3GlcNAc reagent") or a reagent containing a phosphorylated Core M3-modified peptide having added thereto one molecule of ribitol-phosphate (hereinafter referred to as "ribitol-phosphate 1 phosphorylated Core M3-modified peptide reagent") may be selected. An example of the peptide sequence of the phosphorylated Core M3-modified peptide is Ac-AT(Man) PAPVAAIGPK-NH$_2$ (SEQ ID NO: 2). An example of the reagent containing a sugar donor is a reagent containing CDP-ribitol (hereinafter referred to as "CDP-ribitol reagent"). As the reagent containing an enzyme source, a reagent containing secretion-type FKRP (hereinafter referred to as "secretion-type FKRP reagent") may be used. For example, when only FKRP activity in a specimen is to be assayed, the secretion-type FKRP reagent may not be used. In addition, in, for example, the case of confirming the activity of a compound that influences the activity of FKRP, the secretion-type FKRP reagent may be used. The secretion-type FKRP reagent may also be used as an authentic enzyme sample for FKRP.

The dystroglycan glycan may be analyzed using cells deficient or mutated in a gene for any one of ISPD, fukutin, and FKRP. The cells deficient or mutated in a gene for any one of ISPD, fukutin, and FKRP may be generated by a technique such as genome editing. Cells deficient in the gene or cells mutated in the gene may be generated. In addition, in place of the cells deficient or mutated in a gene for any one of ISPD, fukutin, and FKRP, cells derived from a patient accompanied by abnormal glycosylation of dystroglycan may also be used. The glycan state of dystroglycan may be confirmed by adding CDP-ribitol (alone, or a mixture with a nucleic acid transfection reagent) to the cells deficient or mutated in a gene for any one of ISPD, fukutin, and FKRP, or the cells derived from a patient accompanied by abnormal glycosylation of dystroglycan, culturing the cells, and then collecting the cells. When a candidate compound considered to have an effect on the formation of the glycan of dystroglycan is allowed to act on such assay system, the effect of the candidate compound may be tested using the glycan state of dystroglycan as an indicator. The glycan state of dystroglycan may be confirmed by applying a method known per se, such as a western blot method or an immunostaining method, or by applying a method to be developed in the future.

EXAMPLES

The present invention is described in detail below by way of Reference Examples and Examples for a better understanding of the present invention. However, the present invention is by no means limited to these Examples.

Reference Example 1

In this Reference Example, the details of the structural analysis of a dystroglycan glycan, which has led to the completion of the present invention, and the preparation of dystroglycan for mass spectrometry for the analysis of the glycan structure are described.

For the purpose of the structural analysis of the dystroglycan glycan, it was difficult to secure a sample amount required for the analysis from a biological tissue. Meanwhile, with regard to a recombinant capable of securing a large sample amount, there were also problems in that: even when cultured cells were caused to express recombinant dystroglycan, the efficiency with which the recombinant dystroglycan was modified with a glycan having physiological activity similar to that of dystroglycan in a biological tissue was extremely low; and the recombinant dystroglycan had a glycan structure different from that in a living body. Further, another factor making the glycan analysis difficult was that dystroglycan had about 40 sites of serine/threonine residues at which glycosylation could occur, and had high nonuniformity in glycosylation.

In view of the foregoing, first, a search was made for a cell line capable of modifying recombinant dystroglycan with a physiological glycan similar to that of dystroglycan in a biological tissue. As a result, it was found that, in NIH3T3 cells, recombinant dystroglycan was modified with a physiological glycan with high efficiency.

On the basis of the foregoing, a recombination operation was employed to design wild-type (WT) dystroglycan limited to an N-terminal globular domain (amino acid No. 1 to 313) of dystroglycan and 20 amino acids (amino acid No. 314 to 333 of dystroglycan) including a total of five serine and threonine residues at glycosylation positions (present in a mucin domain subsequent to the N-terminal globular domain). In the maturation process of dystroglycan, the N-terminal globular domain is subjected to cleavage processing at amino acid 310, and hence is not present in mature dystroglycan used in the analysis. That is, the dystroglycan used for analysis is constituted of amino acid No. 311 to 333. Separately, a mutant (T190M) in which amino acid 190 in the N-terminal globular domain of dystroglycan was mutated from threonine to methionine was also created. The mutation site at position 190 is not included in the glycosylation domain, but the mutant mutated at position 190 is not modified with part of the physiological glycan, specifically, a repeating structure (Xyl-GlcA repeat) containing a disaccharide of xylose (Xyl) and glucuronic acid (GlcA) as a unit. Further, a mutant (T320K) capable of being more fragmented by lysine-cleaving enzymatic treatment, in which amino acid 320 was mutated from threonine to lysine by introducing a lysine residue into the sequence of 20 amino acids, was also created. Recombinant dystroglycan not particularly limited to, for example, the wild type or a mutant type is hereinafter referred to simply as "rDG", the wild-type dystroglycan whose glycosylation positions are limited to 20 amino acids (amino acid No. 314 to 333 of dystroglycan) is hereinafter referred to as "$DG^{WT}$", and each mutant dystroglycan is hereinafter referred to as "$DG^{T190M}$" or "$DG^{T320K}$". Those recombinant dystroglycans including an Fc tag serving as a PreScission cleavage sequence at the C-terminus are respectively referred to as "DGFc", "$DGFc^{WT}$", "$DGFc^{T190M}$", and "$DGFc^{T320K}$".

An NIH3T3 stable expression cell line expressing rDG was established. As a result, $DG^{WT}$ and $DG^{T320K}$ were each confirmed to be modified with a physiological glycan, but $DG^{T190M}$ did not undergo physiological glycosylation.

The rDG stable expression NIH3T3 cells were cultured in a BelloCell™ culture apparatus for 1 week, and the culture supernatant was collected. DGFc was collected from the culture supernatant using Protein A-beads. Then, the Fc tag portion was cleaved by PreScission enzyme treatment, the Fc tag portion was removed with Protein A-beads, and PreScission Protease was removed with glutathione-beads. The rDG also contains glycans other than the glycan having physiological activity. However, sialic acids and O-GalNAc-type glycans were removed by O-glycosidase treatment and α2,3,6,8,9-neuraminidase treatment. Further, the rDG was fractionated by ammonium acetate elution (stepwise elution of 0.1 M, 0.25 M, 0.5 M, and 0.75 M) through an ion-exchange column, and was used as a sample for glycan structure analysis.

The glycan structure analysis was performed by mass spectrometry using MALDI-TOF. As a mass spectrometer, a MALDI-TOF mass spectrometer (Applied Biosystems) was used. For $DG^{WT}$, signals at an interval corresponding to a mass of 308, representing modification with the Xyl-GlcA repeat, were detected in a high-concentration ammonium acetate elution fraction, and hence it was revealed that $DG^{WT}$ was modified with a physiological glycan. Meanwhile, for $DG^{T190M}$, the Xyl-GlcA repeat was not found, but instead, a peak representing a mass of 6,138 was obtained. The glycopeptide having a mass of 6,138 is one not modified with only the Xyl-GlcA repeat structure. The physiologically active glycan is supposed to be bound to a core glycan via a phosphodiester linkage. When the $DG^{WT}$ glycopeptide was treated with hydrogen fluoride for chemically cleaving the phosphodiester linkage, a glycopeptide having a mass of 5,402 was obtained. That is, the presence of a glycan having a mass of 736 obtained as the difference of 6,138-5,402 was found.

The constituent components of the glycan having a mass of 736 were analyzed using a hybrid mass spectrometry system including two analyzers, i.e., a linear ion trap (LTQ) and an electric field-type Fourier transform mass spectrometry mechanism (Orbitrap) (LTQ XL™ ion trap mass spectrometer, Thermo Fisher Scientific), and as a result, it was revealed that one Xyl-GlcA unit, and two units having masses of 134 and 80 were present. Precise mass spectrometry of the components having masses of 134 and 80 found that 134 corresponded to a molecule having the chemical formula $C_5H_{12}O_5$, and 80 corresponded to phosphate. The compound of $C_5H_{12}O_5$ is any one of ribitol, xylitol, and arabitol. Accordingly, the monosaccharide composition of rDG was analyzed using each of the compounds as a standard substance, and as a result, it was revealed that the dystroglycan contained ribitol.

Thus, it was revealed that the structure having a mass of 736 connecting the core glycan and the Xyl-GlcA repeat was ribitol-phosphate-ribitol-phosphate-Xyl-GlcA. In addition, it was confirmed that $DG^{T320K}$ also contained ribitol-phosphate. The presence of ribitol-phosphate had been found only in a very few bacteria and a plant (relative of *Adonis ramosa*), and ribitol-phosphate had not been found in mammals. In view of this, through the following Examples, responsible genes for diseases associated with abnormal glycosylation of dystroglycan and the mechanism for the incorporation of ribitol-phosphate into a glycan were analyzed.

(Example 1) Action of ISPD

In this Example, with regard to ISPD serving as one of the responsible genes for muscular dystrophy, its function in glycosylation of dystroglycan was confirmed.

1. Reaction with Normal ISPD

Figure 2:
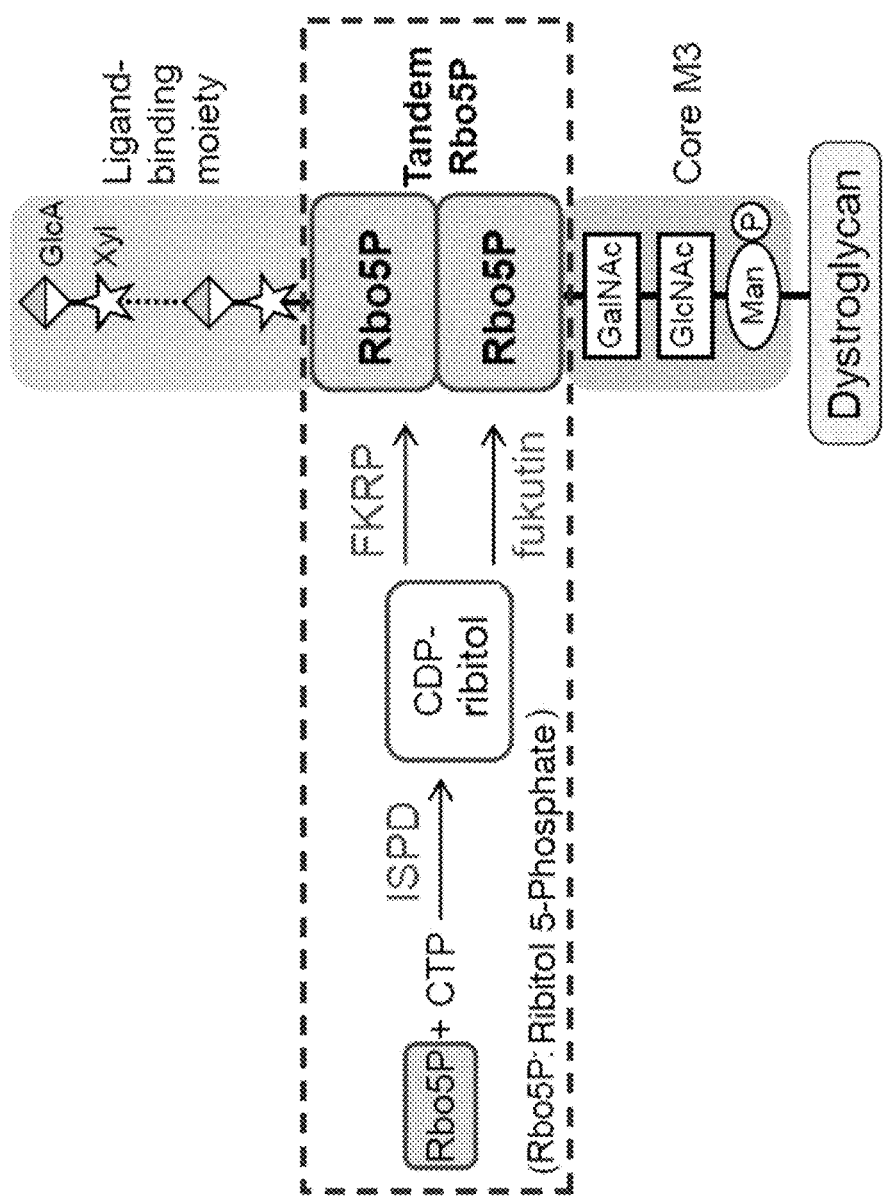
FIG. 2 is a diagram for schematically illustrating the action mechanism of a therapeutic agent for diseases associated with abnormal glycosylation of dystroglycan, containing CDP-ribitol as an active ingredient, of the present invention.
Figure 3:
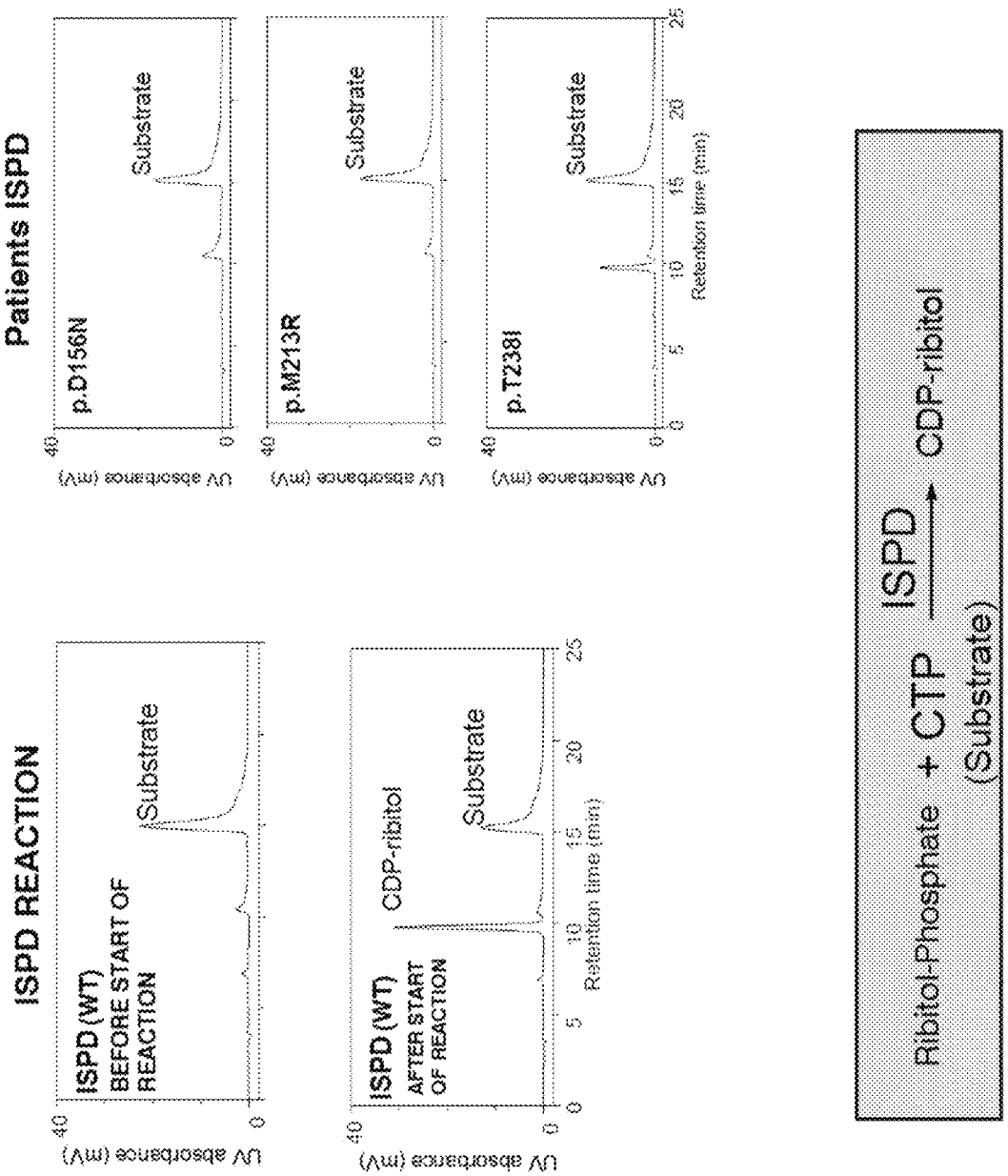
FIG. 3 are graphs obtained by analyzing the function of ISPD given as one of the responsible genes for the disease associated with abnormal glycosylation of dystroglycan (Example 1).

In bacteria, CDP-ribitol is synthesized by a reaction between ribitol-phosphate (ribitol 5-phosphate: Rbo5P) and CTP. In this Example, the action of ISPD was investigated as to whether it was possible to synthesize CDP-ribitol from ribitol-phosphate using CTP as a substrate. His-tagged human ISPD was generated by a recombination operation, and used as an enzyme source. Gene information on human ISPD is disclosed in RefSeq: NM_001101426. The generated human ISPD was mixed with ribitol-phosphate and CTP to cause an enzymatic reaction, and the enzymatic reaction product was analyzed by HPLC. The enzymatic reaction was performed under the following conditions: human ISPD was subjected to a reaction in a total of 40 µl of a reaction solution containing 100 mM MOPS-NaOH (pH 7.4), 10 mM $MgCl_2$, 1 mM CTP, and 2 mM Rbo5P at 37° C. for 2 hours. HPLC was performed using a 4.6×150 mm COSMOSIL™ PBr column (Nacalai Tesque) under the conditions of isocratic elution with 3% methanol/97% triethylamine acetate (pH 7.3) at 30° C., and the enzymatic reaction product was detected at an absorbance of 254 nm. A peak found before the enzymatic reaction was CTP serving as the substrate, whereas after the enzymatic reaction, the peak of CTP decreased and CDP-ribitol was found as a new peak (left of FIG. 3). Thus, it was confirmed that ISPD was a CDP-ribitol synthase (FIG. 2).

2. Reaction with Mutant ISPD

For mutant ISPD according to ISPD-mutated patients (p.D156N, p.M213R, and p.T238I), each recombinant ISPD was generated and an enzymatic reaction was performed in the same manner as in the section 1. The amount of CDP-ribitol serving as the enzymatic reaction product was confirmed. As a result, a peak value representing CDP-ribitol was low as compared to that in the case where the reaction was performed with normal ISPD. It was confirmed that mutant ISPD provided a low synthesis amount of CDP-ribitol (right of FIG. 3).

CDP-ribitol is important as a sugar donor substrate for ribitol-phosphate to be incorporated into a glycan. The results of this Example suggested that, while ISPD allowed the biosynthesis of CDP-ribitol, mutant ISPD caused a problem in the biosynthesis of CDP-ribitol, leading to a disease.

(Example 2) Action of Fukutin

In this Example, with regard to fukutin serving as one of the responsible genes for muscular dystrophy, its function in glycosylation of dystroglycan was confirmed.

1. Reaction with Normal Fukutin

Figure 4:
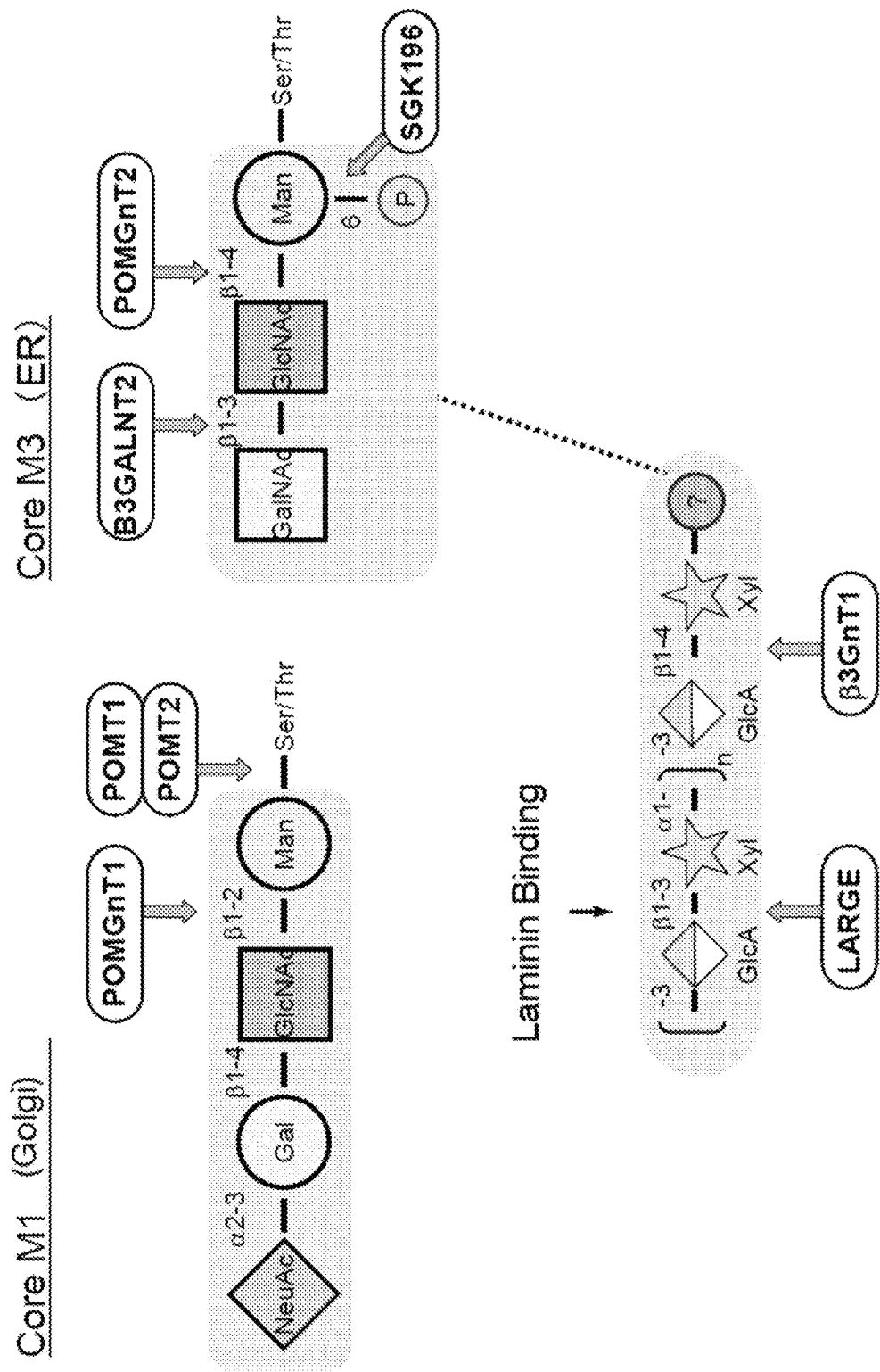
FIG. 4 is a diagram for illustrating the outline of a dystroglycan glycan structure revealed prior to the present invention (Example 2).

The action of fukutin on the synthesis of a dystroglycan glycan was investigated. Human fukutin was generated by a recombination operation. Gene information on human fukutin is disclosed in RefSeq: NM 006731. Fukutin was expressed as a secretion-type recombinant by removing the transmembrane domain. CDP-ribitol serving as a sugar donor substrate (donor for ribitol-phosphate) and a phosphorylated Core M3-modified peptide serving as a sugar acceptor substrate were mixed with the generated secretion-type human fukutin to cause an enzymatic reaction, and the enzymatic reaction product was analyzed by HPLC. The enzymatic reaction was performed under the following conditions: 25 µl of human fukutin bound to agarose beads was subjected to a reaction in a total of 50 µl of a reaction solution containing 100 mM MES (pH 6.5), 0.5 mM CDP-Rbo, 0.1 mM phosphorylated Core M3-modified peptide, 10 mM $MnCl_2$, 10 mM $MgCl_2$, and 0.5% Triton X-100 at 37° C. for 16 hours. The enzymatic reaction product was separated by reversed-phase HPLC using a 5×250 mm Mightysil RP-18GP Aqua column (Kanto Chemical). With the use of 0.1% trifluoroacetic acid (TFA)-containing distilled water as solvent A and 0.1% TFA-containing acetonitrile as solvent B, the enzymatic reaction product was eluted under the conditions of a flow rate of 1 ml/min and a linear concentration gradient of 0%-40% solvent B. The eluate was detected at an absorbance of 214 nm. Herein, Core M3 refers to part of the glycans constituting the dystroglycan glycan, and is formed of GalNAcβ1-3GlcNAcβ1-4Man—(see FIG. 4). The phosphorylation of Man is important for further glycosylation. Herein, the peptide refers to Ac-AT-PAPVAAIGPK-$NH_2$ (SEQ ID NO: 1). This peptide mimics the sequence of dystroglycan, but contains only one threonine residue. Man-modified threonine is used in synthesis, and hence Ac-AT (Man) PAPVAAIGPK-$NH_2$ (SEQ ID NO: 2) is obtained. The Man-modified peptide of SEQ ID NO: 2 serving as a starting material was subjected to stepwise enzymatic reactions with POMGNT2, B3GALNT2, and POMK to prepare a phosphorylated Core M3-modified peptide. Before the fukutin enzymatic reaction, only the peak of the phosphorylated Core M3-modified peptide serving as the sugar acceptor substrate was found (left figure of FIG. 5, before reaction), whereas after the reaction, the peak of the phosphorylated Core M3-modified peptide decreased and the peak of Product 1 was newly found (left figure of FIG. 5, after reaction).

Figure 5:
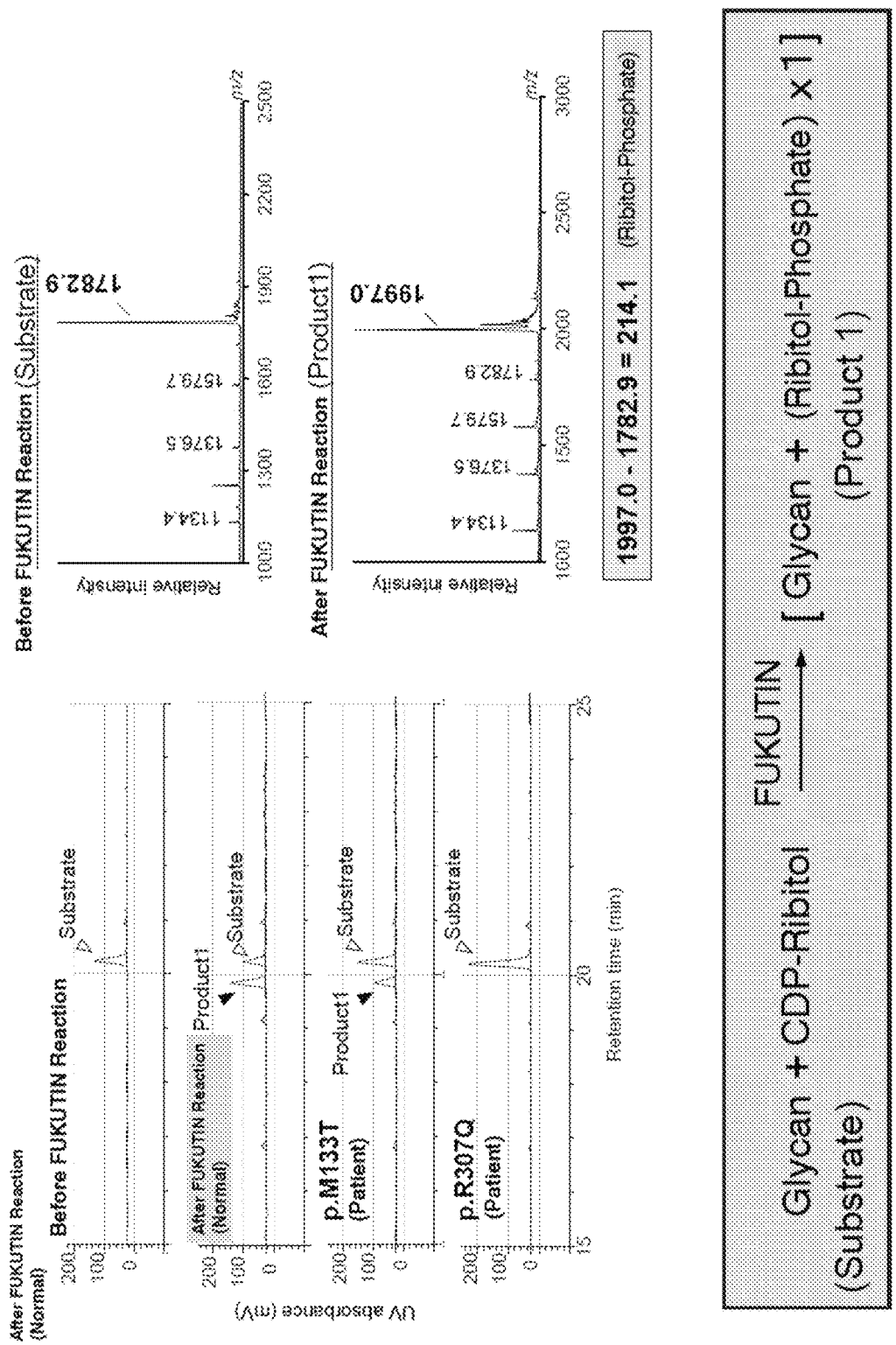
FIG. 5 are graphs obtained by analyzing the function of fukutin given as one of the responsible genes for the disease associated with abnormal glycosylation of dystroglycan (Example 2).

The structure of the Product 1 was analyzed by mass spectrometry, and as a result, it was confirmed that Product 1 was a phosphorylated Core M3-modified peptide containing one molecule of ribitol-phosphate (second from the top left of FIG. 5). Thus, it was confirmed that human fukutin was an enzyme for incorporating ribitol-phosphate from CDP-ribitol into a glycan, namely a ribitol transferase (FIG. 2).

2. Reaction with Mutant Fukutin

For mutant fukutin according to fukutin-mutated patients (p.M133T and p.R307Q), secretion-type recombinant fukutin was generated in the same manner as in the section 1, and an enzymatic reaction was performed in the same manner. In the case of p.M133T mutant fukutin, a peak amount representing Product 1 as the enzymatic reaction product was low as compared to that in the case of normal fukutin (third from the top left of FIG. 5), and in the case of p.R307Q mutant fukutin, the peak representing Product 1 was unable to be confirmed (fourth from the top left of FIG. 5). That is, it was confirmed that mutant fukutin had reduced ribitol-phosphate transferase activity.

The enzymatic reaction product was analyzed by nuclear magnetic resonance (NMR) to identify a position to which ribitol-phosphate was bound. The analysis was performed by one-dimensional $^1$H-$^{13}$C (HSQC) and two-dimensional $^1$H-$^{31}$P (HMBC). The results suggested that fukutin was a transferase for transferring Rbo5P from CDP-ribitol to the GalNAc-3 position in a glycan to synthesize a glycan (GalNAc-3 Rbo5P transferase).

(Example 3) Action of FKRP

In this Example, with regard to FKRP serving as one of the responsible genes for muscular dystrophy, its function in glycosylation of dystroglycan was confirmed.

1. Reaction with Normal FKRP

Figure 6:
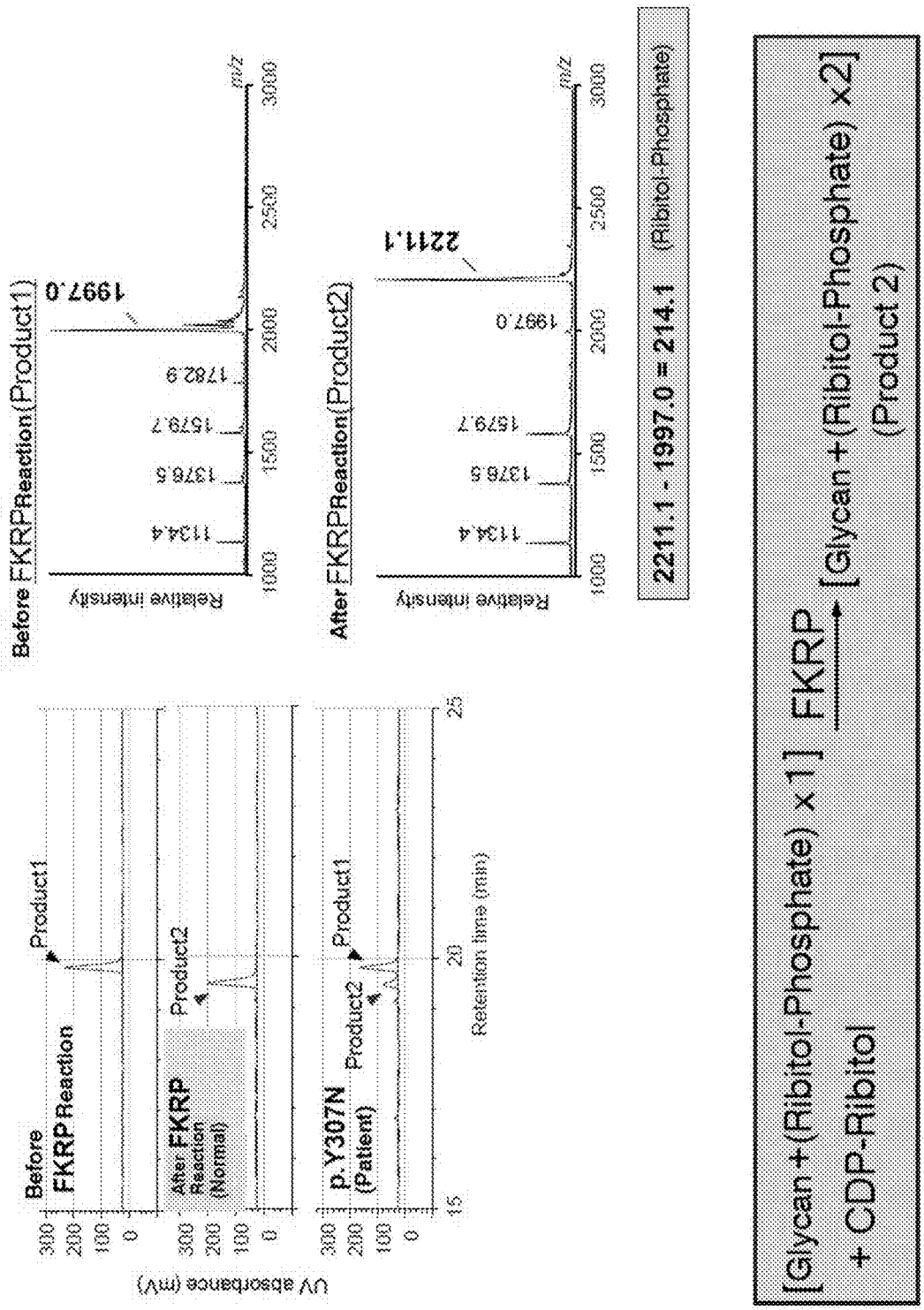
FIG. 6 are graphs obtained by analyzing the function of FKRP given as one of the responsible genes for the disease associated with abnormal glycosylation of dystroglycan (Example 3).

The action of FKRP on the synthesis of a dystroglycan glycan was investigated. Human FKRP was generated by a recombination operation. Gene information on human FKRP is disclosed in RefSeq: NM 024301. In the same manner as in Example 2, FKRP was expressed as a secretion-type recombinant by removing the transmembrane domain. In the same manner as in Example 2, CDP-ribitol serving as a sugar donor substrate (donor for ribitol-phosphate), and the glycopeptide containing one molecule of ribitol-phosphate (Product 1) generated in Example 2 serving as a sugar acceptor substrate were mixed with the first generated secretion-type human FKRP to cause an enzymatic reaction, and the enzymatic reaction product was analyzed by HPLC (FIG. 6). The enzymatic reaction was performed under the following conditions: 25 µl of human FKRP bound to agarose beads was subjected to a reaction in a total of 50 µl of a reaction solution containing 100 mM MES (pH 6.5), 0.5 mM CDP-Rbo, 0.1 mM ribitol-phosphate-phosphorylated Core M3-modified peptide, 10 mM MnCl$_2$, 10 mM MgCl$_2$, and 0.5% Triton X-100 at 37° C. for 16 hours. The enzymatic reaction product was separated and eluted by reversed-phase HPLC in the same manner as in Example 2, and the eluate was detected at an absorbance of 214 nm.

Before the reaction, only the peak of Product 1 was found (left figure of FIG. 6, before reaction), whereas after the reaction, the peak of Product 2 was newly found instead of the peak of Product 1 (left figure of FIG. 6, after reaction). The peak of the Product 2 was subjected to mass spectrometry, and as a result, it was confirmed that Product 2 was a phosphorylated Core M3-modified peptide containing two molecules of ribitol-phosphate (second from the top left of FIG. 6). Thus, it was confirmed that human FKRP was an enzyme for incorporating ribitol-phosphate from CDP-ribitol into a glycan, namely a ribitol transferase (FIG. 2).

2. Reaction with Mutant FKRP

For p.Y307N mutant FKRP according to an FKRP-mutated patient, secretion-type recombinant FKRP was generated and an enzymatic reaction was performed in the same manner as in the section 1. In the case of mutant FKRP, a peak amount representing Product 2 as the enzymatic reaction product was low as compared to that in the case of normal FKRP, and the peak of Product 1 remained (third from the top left of FIG. 6). That is, it was confirmed that mutant FKRP had reduced ribitol-phosphate transferase activity. The enzymatic reaction product was also subjected to NMR analysis to identify a position to which ribitol-phosphate was bound. It was considered that FKRP was a transferase for transferring Rbo5P from CDP-ribitol to the C1 position of ribitol 5-phosphate in a glycan to synthesize a glycan (CDP-Rbo: Rbo5P-1Rbo5P transferase).

(Example 4) Ribitol-Phosphate Modification in Patient Model Cells

In this Example, modification with ribitol-phosphate in cells deficient in any one of ISPD, fukutin, or FKRP was confirmed. HAP1 cells deficient in each gene were generated using a CRISPR/CAS9 genome editing method, and were used as patient model cells. The deficiency mutation was confirmed by DNA sequencing. The kind of mutation is different from that of an actual patient, but the cells may be called model cells because of the same deficiency in gene function.

Figure 7:
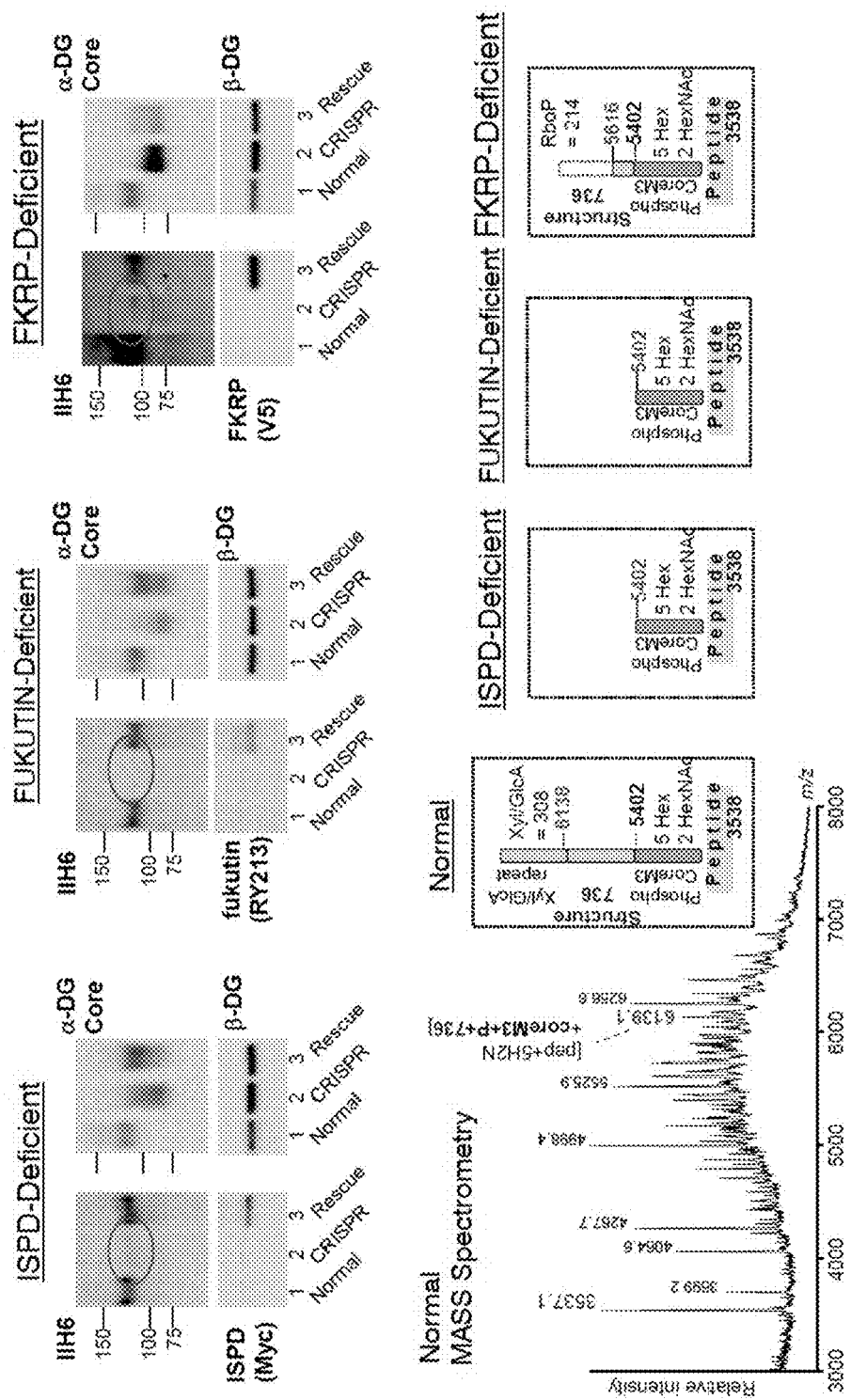
FIG. 7 are images and a graph obtained by generating ISPD-, fukutin-, or FKRP-deficient cells by genome editing, and confirming the biosynthesis of a dystroglycan glycan in the cells (Example 4).

In each of the cells in the upper part of FIG. 7, it was confirmed that the glycan was deficient in each of the deficient cells (CRISPR lane). In addition, when the deficient gene was re-expressed by transfection, the glycan was restored (Rescue lane). Thus, the validity of the generated cells as disease model cells was demonstrated. Those cells were caused to express DG$^{WT}$ in the same manner as in Reference Example 1, and the glycan was analyzed by mass spectrometry. In the normal cells, as shown in the lower left figure, a peak represented by 736 including ribitol-phosphate was detected (FIG. 7). In the cells deficient in ISPD or fukutin, the peak represented by 736 was not detected because the transfer of ribitol-phosphate to the glycan did not occur. Meanwhile, in the FKRP-deficient cells, the first ribitol-phosphate molecule was incorporated, and hence a glycan containing one molecule of ribitol-phosphate, which was part of the molecule represented by 736, was detected. Thus, it is considered that results supporting the glycan structure data and enzymatic activity data shown in Examples 1 to 3 were obtained. In addition, this revealed that the abnormality in ISPD, fukutin, or FKRP prevented in vivo ribitol-phosphate modification from occurring sufficiently, resulting in the development of the disease associated with abnormal glycosylation of dystroglycan.

(Example 5) Amelioration of Abnormal Glycosylation by CDP-Ribitol Administration The results of Examples 1 and 4 have revealed that ISPD-deficient patients cannot biosynthesize CDP-ribitol in cells, and the abnormality in in vivo ribitol-phosphate modification results in the development of the disease associated with abnormal glycosylation of dystroglycan. In this Example, for HAP1 cells and HEK cells, cells deficient in ISPD were generated using a CRISPR/CAS9 genome editing method. The HAP1 cells are a haploid cell line derived from cultured human leukemia cells (KBM7), and are cells capable of being subjected to genome editing with high efficiency.

Figure 8:
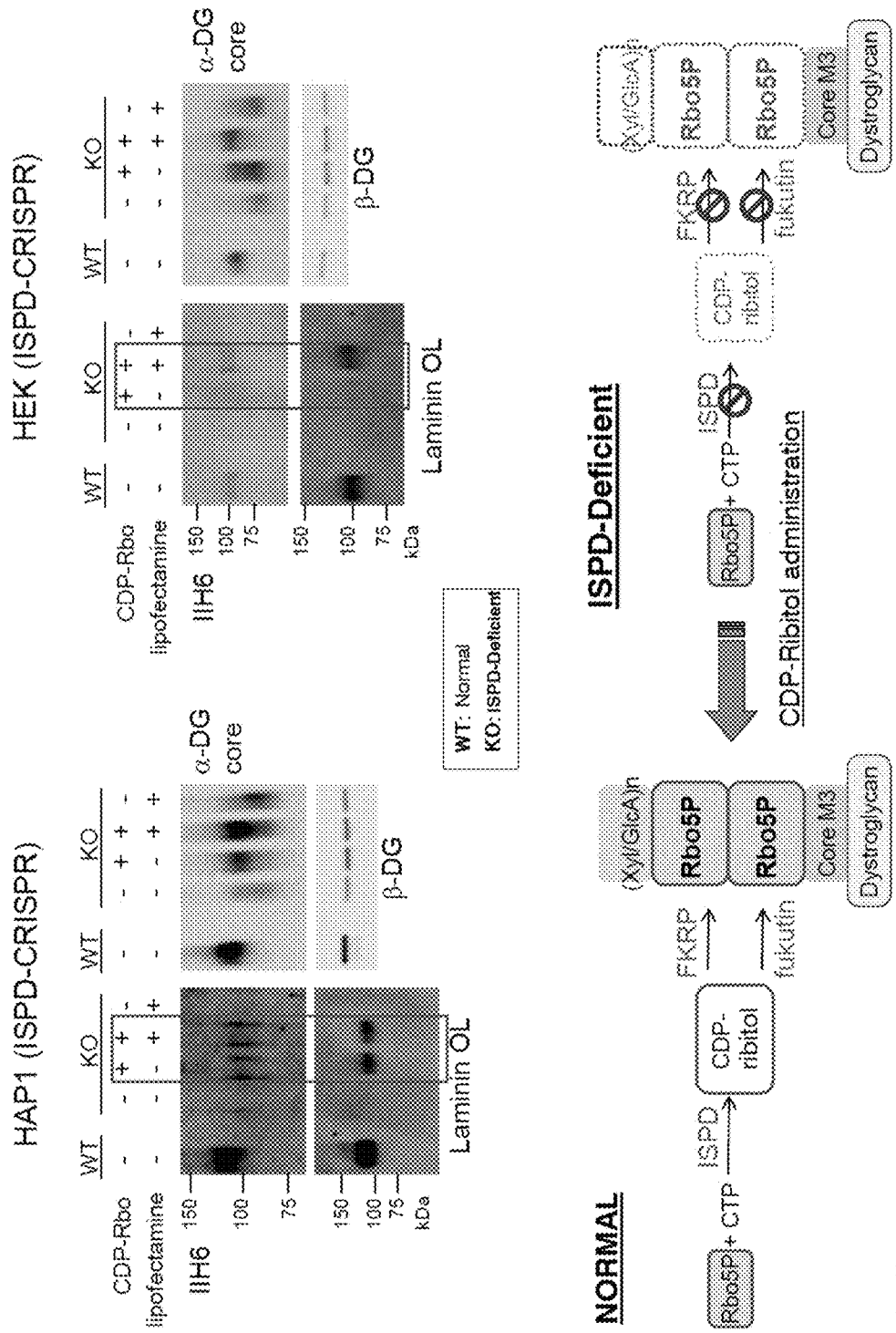
FIG. 8 are images and a diagram obtained by generating ISPD-deficient cells by genome editing, and confirming that the addition of CDP-ribitol has restored a dystroglycan glycan (Example 5).

For the HAP1 cells and HEK cells of FIG. 8, in this Example, WT represents normal cells not deficient in ISPD, and KO represents ISPD-deficient cells in which ISPD has been knocked out by a CRISPR/CAS9 genome editing method. The deficiency mutation of the ISPD-deficient cells was confirmed by DNA sequencing. To each culture medium, CDP-ribitol was added at a final concentration of 1 mM, followed by culture for 24 hours. After the culture, cell endogenous dystroglycan was prepared from a cell extract, and the state of glycosylation was confirmed by a western blot method. In the case of the HAP1 cells, it is considered that, even in the ISPD-deficient cells, the extracellular addition of CDP-ribitol caused glycosylation of α-DG similar to that in the normal cells, to thereby restore the synthesis of the glycan. In addition, in the case of the HEK cells, when CDP-ribitol was administered to the ISPD-deficient cells simultaneously with a cell transfection reagent (lipofectamine™), the restoration of the glycan was confirmed. That is, it was suggested that, in the ISPD-deficient cells, supplementation with CDP-ribitol restores the synthesis of the glycan, and hence serves as effective therapy.

INDUSTRIAL APPLICABILITY

As described in detail above, the therapeutic agent for diseases associated with abnormal glycosylation of dystroglycan, containing CDP-ribitol as an active ingredient, ameliorates the abnormal glycosylation, and as a result, effectively acts on the treatment of the disease and/or the amelioration of symptoms associated with the disease. The actions of the causative genes for the disease associated with abnormal glycosylation of dystroglycan have been confirmed, and the cause of the development of the disease has been elucidated. Thus, a contribution can be made to the development of a more effective therapeutic method for the target disease.

In the case of a patient with a mutation in fukutin or FKRP, it is considered that the enzymatic activity of fukutin or FKRP does not become zero owing to the mutation, and a little activity remains (when the activity becomes zero, the patient cannot survive, and hence is not born). In the case where even a little activity of fukutin or FKRP remains, when CDP-ribitol serving as a material for the enzymatic reaction of fukutin or FKRP is present in a large amount, the transfer and incorporation of ribitol-phosphate into the dystroglycan glycan is considered to proceed through the utilization of the remaining enzymatic activity. That is, CDP-ribitol supplementation therapy can be expected to exhibit an effect on not only the abnormality in the ISPD gene, but also the abnormality in the fukutin gene or the abnormality in the FKRP gene. In addition, even in the case of a gene other than ISPD, fukutin, and FKRP, as long as the gene influences ribitol-phosphate in glycosylation of dystroglycan, the therapeutic agent containing CDP-ribitol as an active ingredient of the present invention can effectively act also on a disease associated with abnormal glycosylation of dystroglycan caused by an abnormality in such gene.

The invention claimed is:

1. A method for treating a patient having a disease associated with abnormal glycosylation of dystroglycan, said method comprising administering a formulation that comprises CDP-ribitol to said patient.

2. The method of claim 1, wherein the disease occurs in association with an abnormality in any one gene selected from ISPD, FKRP, fukutin, POMT1, POMT2, DAG1, LARGE, DPM1, DPM2, DPM3, B3GALNT2, GMPPB, TMEM5, POMK, DOLK, POMGNT1, POMGNT2, and B4GAT1.

3. The method of claim 1, wherein the abnormal glycosylation of dystroglycan comprises an abnormality in ribitol-phosphate in a dystroglycan glycan.

4. The method of claim 1, wherein the disease associated with abnormal glycosylation of dystroglycan comprises α-dystroglycanopathy.

5. The method of claim 4, wherein the α-dystroglycanopathy comprises any one selected from Fukuyama muscular dystrophy, Walker-Warburg syndrome, muscle-eye-brain disease (MEB), limb-girdle muscular dystrophy type 2I, limb-girdle muscular dystrophy type 2M, and cardiomyopathy.

6. The method of claim 1, wherein the disease associated with abnormal glycosylation of dystroglycan comprises a disease that causes an abnormality in biosynthesis of a laminin-binding glycan in association with an abnormality in an ISPD gene.

7. The method of claim 1, wherein the disease occurs in association with a mutation in any one gene selected from FKRP and fukutin.

8. The method of claim 1, wherein the CDP-ribitol is administered to the patient at a dosage from 0.01 mg to 60 g.

9. The method of claim 1, wherein the CDP-ribitol is administered to the patient at a dosage from 0.01 mg to 24 g.

10. The method of claim 1, wherein the CDP-ribitol is administered to the patient at a dosage from 0.01 mg to 6 g.

* * * * *

```
                           SEQUENCE LISTING

<160> NUMBER OF SEQ ID NOS: 8

<210> SEQ ID NO 1
    <211> LENGTH: 12
    <212> TYPE: PRT
    <213> ORGANISM: Artificial
    <220> FEATURE:
    <223> OTHER INFORMATION: Synthesized glycopeptide of CoreM3

<400> SEQUENCE: 1

Ala Thr Pro Ala Pro Val Ala Ala Ile Gly Pro Lys
    1               5                   10

<210> SEQ ID NO 2
    <211> LENGTH: 12
    <212> TYPE: PRT
    <213> ORGANISM: Artificial
    <220> FEATURE:
    <223> OTHER INFORMATION: Synthesized glycopeptide of CoreM3
    <220> FEATURE:
    <221> NAME/KEY: CARBOHYD
    <222> LOCATION: (2)..(2)
    <223> OTHER INFORMATION: Man

<400> SEQUENCE: 2

Ala Thr Pro Ala Pro Val Ala Ala Ile Gly Pro Lys
    1               5                   10

<210> SEQ ID NO 3
    <211> LENGTH: 7364
    <212> TYPE: DNA
    <213> ORGANISM: Homo sapiens

<400> SEQUENCE: 3
```

```
gtaaagcgga gcggctgcag cctgctgttg agtgagaaaa caaaattatc ttccttccca      60
aatccaaaaa gatgaaaacg actgagatac tttcaaagag caaccaagtg agcagcacag    120
actaatgagt agaatcaata agaacgtggt tttggccctt ttaacgctga caagttctgc    180
atttctgctg tttcagttgt actactacaa gcactattta tcaacaaaga atggagctgg    240
tttgtcaaaa tccaaaggaa gccgaattgg atttgatagc acacagtggc gtgcagttaa    300
aaaatttatt atgttaacat ccaaccaaaa tgtaccagtg tttcttattg atcctttgat    360
actggaattg attaataaga actttgaaca agtcaaaaat acttctcatg gctctacttc    420
acaatgcaag ttttctgtg ttccaagaga ctttactgca tttgcactgc agtatcacct     480
atggaagaat gaggaaggct ggtttcggat agctgagaat atgggatttc agtgcctaaa    540
gattgagagt aaagatcccc ggctagacgg atagactca ctctctggaa ctgaaatccc      600
cctgcactat atctgcaaac tggccactca tgcgatccac ttggtagtct ttcatgagag    660
gagtggcaac tacctctggc acggccactt gagacttaaa gaacacattg acaggaaatt    720
tgttcccttc cgaaagttac agtttggtcg ttatccagga gcttttgaca ggccagagtt    780
acagcaagtt actgttgatg gactggaagt tctcattcca aaggatccaa tgcactttgt    840
agaagaagta ccacactcta ggtttattga gtgtaggtat aaagaagctc gagcattctt    900
tcagcagtac cttgatgata acactgtgga agctgtggcc tttcggaaga gtgcaaagga    960
attactgcaa ctagcagcga aaacattaaa caaattggga gtaccattct ggctgagcag   1020
tggaacttgt ctaggatggt atcgacaatg caacattatt ccttatagca agatgttga    1080 cctaggaatt tttatacaag attacaaatc tgatattatt ttagcatttc aggatgcagg   1140
acttccgctc aaacacaaat ttgggaaggt agaagacagc ttggaactat ccttccaggg   1200
aaaagatgat gtaaaacttg atgttttttt cttctatgaa gaaactgatc acatgtggaa   1260
tggaggcact caggccaaaa caggaaaaaa attcaaatac ctgtttccga gtttacact    1320 gtgctggact gagtttgtag acatgaaggt ccatgtaccc tgtgaaaccc tcgaatacat   1380
tgaagccaac tatggtaaga cctggaagat tcctgtaaag acgtgggact ggaagcgctc   1440
tcctcccaat gtgcaaccca tggaatctg gcctatttct gagtgggatg aggttatcca    1500
gttatattga gatagtaggt tgaaatggga gaatttctct tttggaaaaa aaggtagata   1560 actgttaaa aaatacatgt ctatttgtca aacataagtg ggaaccaaag aaaaaatgtg    1620
acaagtttga agacacagaa agagtcatct gatgtaattc tctcacttag tactgaggaa   1680
ttttcatgtg ccacatacaa tgctaggtta cagtggagaa gcctagatga atgagacaaa   1740
tacctacttc ttttattcct ccttttggta aacaactcaa ttttcctttg agggaaccct   1800
cccccaccct ttgaagagtt caagttctgt acaggttttt aaaacgtgaa gtaatgtttg   1860
aactggaaga tgagctcacc aggcaaagct aaggaaggat atactagttg aaaagaataa   1920
cccactcctc ttctgggcat ttaagctggt atgttagtgc tacttttaag attgtggagt   1980
ctgagttaat attcaagtga tcagactttg agtgacatca agaaaagatg atatcaggtt   2040 cattttcaa ctaatcttat gtggaattga attagagaac aaggcattat tcttttaggg    2100
aaggtgagag cttatttgta tcagagctta ttacttgtca ggataagtaa atttctgtac   2160
atgtactgtt ttcatatgtg aagtgagaag aaacttatg cttgtttaat gcttaaattt    2220
ccatccattg tgagaatatt ttcactgacc tctgatggca cttgttgaca aatcattcaa   2280
gtgagaccat gttactagac atgatcttga aagaggccat gatttcacaa aactcatttt   2340
```

```
tattttattc tcagacagtc tgttaggtaa aaatatgaga aattcatgta catttttatat    2400 tttctgaatt tataatctgt gcactcccaa ttttaatgac actaaaatat taatagaatt    2460
ttttaaatat actctaattt ttaaaacata ctctttatta tcttcattta tcaattacag    2520
cttcgtatct ctaatttatg gtctatatac caatttaaat ggcatgtaaa cctgcctgtt    2580
tcttctcctc ttctaatata tcagatctcc aaaatggaag ctaaatggtg gacttgacaa    2640
ctattcaccc tacctcagat catagagttt gtaaagtttg tgtccctccc cagttttca    2700 gtctgttgaa tgtcgatggg gcaagaactc agacttctac tttaccaagt accacacact    2760
ctggaatgct ttagtttcct ttccctca agatgtctga gtcagctagg atgctgttta    2820
ccccatctct ctcttatatc acttgaatga tatattgtaa gtgagaggta aaggaaaatg    2880
taggcacaat aagcactgct attttctct ttgtctagga aaggaagctg aatcttatat    2940
cttatctatg ctatttagga ctactttctg gagcttggca gattttcctc tgacaccaga    3000
gaacaatagt agtctcaaga atggaaacct gaatgtctga gggaatgggc tggtagactt    3060
tttcgaaaac aaattagaga aagtaactta caaccaccca ttccggattt gtaaagcaac    3120
atgaaaacct ttgataaatg ataaccaaca gtcttctgtc ctaatttgca ttctcaatgc    3180
agaattattg ggtcttcat aaataacatg agtggtttct ggagacattt aagattgtca    3240
gcaaacttgt cccaaaatgg cacatcatca taatccattt tctctttgct agaaaatcag    3300
cccatagagt gcattcccaa attctaaata gctgacccta aattcatttt tcatgcttaa    3360
aaataataga acaaataata atactatttt tgggcaaaat ccaccctact tgatgaggac    3420
catttgcttg tgctcagtat ttagaaatgc atacactcca catttctccc catttccaat    3480
tgggactccc attctttgcc aggagatctt acccatccct tttcagatta atcttttatc    3540 cttttcctgaa gtacaaagtc ttaagagtgt ctgaaatcca agcatccttg gcccaattga    3600
cacaggttct atattcttcc ctacatagac cactggctgc tgaaatactt ttcttgtctt    3660
ctggtttcac aggcttcagc tcatgggttc caccctaact tggggaaaca aaagccttct    3720
ctagaatctg aaggccaggc ttacctctga ttctgattca tccatacttc atcttatgta    3780
ttttaacagt tggggttctgt ggagtgtcca gagaccttgg gttaggtata tccatcttca    3840
gtacctcatt ggatcacttt tctttcatca cttgagtatt ctagcagtca ttctcctaat    3900
ctgaccactt tcaggtttag tttacctggc ttacctgggg aagttgacaa cttgttggta    3960
gttaggcacc catgaatgtc tccagagaca tcctgagagg caagattcct cttaattgat    4020
aaccaggaca accaggtagt cacccagtcc tctctaagca gggagcactt gtccttctct    4080
cctctgctgc agctactgat atctggcccc tggaataaaa ccatagttcc taaaattgag    4140
catccctaag agtagctgct tggtgggaca gctgatttct ttgattccct agctgcaaaa    4200
cctgaaattg accactaggt gacagaatgt ttgccagtat ccccacaaaa caagttaaaa    4260
cttaagtgaa aatcattctg cttttgaatc ttaaaagcta gaaaaaccat aatgtaatat    4320 tcttttttaaa ccctcttatt ttataactaa ataaataatc acagaaaaga atgatctgaa    4380
caagaacagc tgaggctaaa acccaagact gccgtgactc ctagtccaat gtctgtttcg    4440
catcacaaca cagtatcttt aacagtgctt gagatgctta acagagaagg catccagtgc    4500
ttcattgagg ctaagtctca gggtgtttct gccgcttagt atctttttgt tcagattgag    4560
aacctaaggc gacagagagg tcaaggggaa gtattttcta gttcagaatt cagaattctt    4620
aggcaacctt catccttta tctggaaaat gccttctctc cagacaataa gacagttcac    4680
atctggagac atcagccttt ggtacctaat tctctaagct caagatgcat cccattgcca    4740
```

```
ctttaccatt ctatttccca agggaaccat cagcaccaac ctgctaaatg cctgtatttg    4800
aagtctctcc ccttcctgaa gtgaccttt  atgaggctct ttccttccta agggaccttt    4860
ccctggtagt agtggtctca ttcacaaaaa agaataatag atgtaactgg agtcactttg    4920
cagttttcaa gattttttt  ttatctgctt ggctggaaag gagactagag tatctagttt    4980
ttagtattta aactactttt aattatttat attgatactc tctgataaat gcaggtagtt    5040
aagaatagat tgtactcatt cctttttgag tttgtgacct caaaccattg ttttattct    5100 tacacgacta cagtacttca aatggcacat agataggcag gatattacat aggtaagcag    5160
gaatttatac attgggtacc agagctaaat ctggaaaaca catttggaat gagcttccac    5220
acttcagtct aaaatctcac ccaaacttat ggctacatat ttttctaagt ttcccccta    5280 gtttcacttt ctggaaagtg aacagttttt taaatcctaa atgttataaa tccttaggag    5340
aaatattccc tcaaaaccta gtcaagaaag tgccacattc ccaccttcta acaggtaatt    5400
attagttgta atagctttaa tgcatggaaa aacttcagtt actgaccagt caagagaatt    5460
tctcaagaaa aatcccagca acgttccctc tttcctcctt gtcttccact atcattaaga    5520
cctgggctag atcacctcta acatctcact cagggaaggc aatgtgttgc cataaaaaga    5580
ccacaagctt ttgagttagg cctgaatttg aatttcagct taatcatgtg ggatttatgg    5640
tggggcccct ttcagtctca atttccacat tagtgaactg gggaaatgat acatacttct    5700
aagggttttt aggggggatta atgaagtat  acagttctta gcctcaggcc taggattaag    5760
taagtactca agaaatgtgc aatttttctag ttccatgttt cttttctaat cttcaaatgg    5820
aattatagaa accatgggtc agaacatatt cctttactca aaagattgca tgactgaatt    5880
tgcttaagaa aaaaaaatt  gtatcaagtc attaatacaa ttatacatta attatattac    5940
attaatacaa tatatggttt gtgaattcag agacattacc agtttgcctc cttctctcaa    6000
tagaacttgt atttcatt  tcttggttaa gcagttgtct cctaatatta tcccatatgc    6060
tacctagttt gctggtccca agcagtttac tgtacttcac tagatttggt acctgctctc    6120
ccctggactt ctttttcaat attctagcct ttcctagatg taaatctta cctccttgtt     6180 agtgaaatta gatataagcc atgatttgga gagggaagaa atctggaata cttaatttca    6240
tttaattatc tatgctgatg aatgcctgta tcattgttaa taaaggagaa ttgaaaatac    6300
tcatttctac tttctgccct caaatttctg tttctatctc aactaggcaa gaatcagcag    6360
ggtgcatgat gccattttaa gctgcttcac atcagactga aatcctaatt acagttcata    6420
agtgaaacag actaattcaa tggcaatacc ttttgtatag gtcctgtgct taaaggaggc    6480
aagtataaat tttctaataa gaaatccctg cttcttttgg gtgcagtggc tcacacctgt    6540
aataccagca gtttgagaag ctaaggcagg tggatcactt gaggccagga gttcgagacc    6600
agcctggcca acatagtgaa acccgtctc  ttctaaaaat acaaaaaaat tagctgggca    6660
tggtggtgca cgcctatagt cccagctaca caggaggctg aggcaggaga atcacttgaa    6720
cccgggaagc agagtctgca gtgagccaag atcgcggcat tgcacttcag cctgggcgat    6780
agagcaagac tctgtctcag aaaaaaaaaa aaaggaaaga aagaaatctc tgcttccgta    6840
ctatcaaaac ttctacccta gaatacccc  tggcaccttc taacccaacc taatacagag    6900
attttgtagg gacccattaa caagctccta tataattata agcagctctc acagtagggt    6960
tgaaagagaa tataaggaaa attagaagta ctgtattttt gctattggaa atgaaatatt    7020
gtttcatgca cctttgaaaa aaataacagg attttacagc cttctgatga ttcattcaaa    7080
```

```
gcatgggaa tagttcatat gtttgttaaa tgaaaatctt atgtagctat ttgtgtgtcc    7140
ctcccacttc ataactacaa aaacatatat atgaatttct aaacaaagtg atattttaaa    7200
gatgaattga ttcaatgtgt acttaccagt ttactgtgtg gttttatctt caggtacaga    7260
tagtttgtgg tactacttga aaatacctt aatattattt tcatcagaat ttgtaatata    7320
taatccagtt tgggatgatg aataaaattt ttctaatctc ttga                    7364
```

<210> SEQ ID NO 4
<211> LENGTH: 461
<212> TYPE: PRT
<213> ORGANISM: Homo sapiens

<400> SEQUENCE: 4

```
Met Ser Arg Ile Asn Lys Asn Val Val Leu Ala Leu Leu Thr Leu Thr
1               5                   10                  15

Ser Ser Ala Phe Leu Leu Phe Gln Leu Tyr Tyr Tyr Lys His Tyr Leu
            20                  25                  30

Ser Thr Lys Asn Gly Ala Gly Leu Ser Lys Ser Lys Gly Ser Arg Ile
        35                  40                  45

Gly Phe Asp Ser Thr Gln Trp Arg Ala Val Lys Lys Phe Ile Met Leu
    50                  55                  60

Thr Ser Asn Gln Asn Val Pro Val Phe Leu Ile Asp Pro Leu Ile Leu
65                  70                  75                  80

Glu Leu Ile Asn Lys Asn Phe Glu Gln Val Lys Asn Thr Ser His Gly
                85                  90                  95

Ser Thr Ser Gln Cys Lys Phe Phe Cys Val Pro Arg Asp Phe Thr Ala
            100                 105                 110

Phe Ala Leu Gln Tyr His Leu Trp Lys Asn Glu Glu Gly Trp Phe Arg
        115                 120                 125

Ile Ala Glu Asn Met Gly Phe Gln Cys Leu Lys Ile Glu Ser Lys Asp
    130                 135                 140

Pro Arg Leu Asp Gly Ile Asp Ser Leu Ser Gly Thr Glu Ile Pro Leu
145                 150                 155                 160

His Tyr Ile Cys Lys Leu Ala Thr His Ala Ile His Leu Val Val Phe
                165                 170                 175

His Glu Arg Ser Gly Asn Tyr Leu Trp His Gly His Leu Arg Leu Lys
            180                 185                 190

Glu His Ile Asp Arg Lys Phe Val Pro Phe Arg Lys Leu Gln Phe Gly
        195                 200                 205

Arg Tyr Pro Gly Ala Phe Asp Arg Pro Glu Leu Gln Gln Val Thr Val
    210                 215                 220

Asp Gly Leu Glu Val Leu Ile Pro Lys Asp Pro Met His Phe Val Glu
225                 230                 235                 240

Glu Val Pro His Ser Arg Phe Ile Glu Cys Arg Tyr Lys Glu Ala Arg
                245                 250                 255

Ala Phe Phe Gln Gln Tyr Leu Asp Asp Asn Thr Val Glu Ala Val Ala
            260                 265                 270

Phe Arg Lys Ser Ala Lys Glu Leu Leu Gln Leu Ala Ala Lys Thr Leu
        275                 280                 285

Asn Lys Leu Gly Val Pro Phe Trp Leu Ser Ser Gly Thr Cys Leu Gly
    290                 295                 300

Trp Tyr Arg Gln Cys Asn Ile Ile Pro Tyr Ser Lys Asp Val Asp Leu
305                 310                 315                 320

Gly Ile Phe Ile Gln Asp Tyr Lys Ser Asp Ile Ile Leu Ala Phe Gln
```

```
                    325                 330                 335
Asp Ala Gly Leu Pro Leu Lys His Lys Phe Gly Lys Val Glu Asp Ser
            340                 345                 350

Leu Glu Leu Ser Phe Gln Gly Lys Asp Asp Val Lys Leu Asp Val Phe
        355                 360                 365

Phe Phe Tyr Glu Glu Thr Asp His Met Trp Asn Gly Gly Thr Gln Ala
    370                 375                 380

Lys Thr Gly Lys Lys Phe Lys Tyr Leu Phe Pro Lys Phe Thr Leu Cys
385                 390                 395                 400

Trp Thr Glu Phe Val Asp Met Lys Val His Val Pro Cys Glu Thr Leu
                405                 410                 415

Glu Tyr Ile Glu Ala Asn Tyr Gly Lys Thr Trp Lys Ile Pro Val Lys
            420                 425                 430

Thr Trp Asp Trp Lys Arg Ser Pro Pro Asn Val Gln Pro Asn Gly Ile
        435                 440                 445

Trp Pro Ile Ser Glu Trp Asp Glu Val Ile Gln Leu Tyr
    450                 455                 460

<210> SEQ ID NO 5
<211> LENGTH: 39
<212> TYPE: PRT
<213> ORGANISM: Artificial
<220> FEATURE:
<223> OTHER INFORMATION: the signal sequence of Gaussia luciferase,
      His/myc tags

<400> SEQUENCE: 5

Met Gly Val Lys Val Leu Phe Ala Leu Ile Cys Ile Ala Val Ala Glu
1               5                   10                  15

Ala Lys Pro Thr His His His His His His Glu Gln Lys Leu Ile Ser
            20                  25                  30

Glu Glu Asp Leu Arg Asn Ser
        35

<210> SEQ ID NO 6
<211> LENGTH: 3422
<212> TYPE: DNA
<213> ORGANISM: Homo sapiens

<400> SEQUENCE: 6
gtcccggcgg ccattgctcc aagatggcgg cggcggcggc agcgggagcg cagctcagct    60
gggctggaac tgccctcctg gaactccccc agcctacaac ctaggagtg cagggactga   120 ggctcaggcc aaatcgcaac tcagacccag tgaacccaag gcctgaagag aatttggatt   180
catttacctt gttttgtggg gactggagag acaagtaaac tctcagagta actgtccct   240 ctgactacca tttctaagga tgccccggag gcccagctag ccccagactt cggccccatg   300
cggctcaccc gctgccaggc tgccctggcg gccgccatca ccctcaacct tctggtcctc   360
ttctatgtct cgtggctgca gcaccagcct aggaattccc gggcccgggg gccccgtcgt   420
gcctctgctg ccggccccg tgtcaccgtc ctggtgcggg agttcgaggc atttgacaac   480
gcggtgcccg agctggtaga ctccttcctg cagcaagacc cagcccagcc cgtggtggtg   540
gcagccgaca cgctccccta cccgccctg gccctgcccc gcatcccaa cgtgcgtctg   600 gcgctgctcc agcccgccct ggaccggcca gccgcagcct cgcgcccgga gacctacgtg   660
gccaccgagt ttgtggccct agtacctgat ggggcgcggg ctgaggcacc tggcctgctg   720
gagcgcatgg tggaggcgct ccgcgcagga agcgcacgtc tggtggccgc cccggttgcc   780
```

```
acggccaacc ctgccaggtg cctggccctg aacgtcagcc tgcgagagtg gaccgcccgc    840
tatggcgcag cccccgccgc gccccgctgc gacgccctgg acgagatgc tgtggtgctc     900 ctgcgcgccc gcgacctctt caacctctcg gcgcccctgg ccggccggt gggcaccagc     960 ctctttctgc agaccgccct tcgcggctgg gcggtgcagc tgctggactt gaccttcgcc    1020
gcggcgcgcc agccccgct ggccacggcc cacgcgcgct ggaaggctga gcgcgaggga     1080
cgcgctcggc gggcggcgct gctccgcgcg ctgggcatcc gcctagtgag ctgggaaggc    1140
gggcggctgg agtggttcgg ctgcaacaag gagaccacgc gctgcttcgg aaccgtggtg    1200
ggcgacacgc ccgcctacct ctacgaggag cgctggacgc cccctgctg cctgcgcgcg    1260 ctgcgcgaga ccgcccgcta tgtggtgggc gtgctggagg ctgcgggcgt gcgctactgg    1320
ctcgagggcg gctcactgct gggggccgcc cgccacgggg acatcatccc atgggactac    1380
gacgtggacc tgggcatcta cttggaggac gtgggcaact gcgagcagct gcgggggca     1440 gaggccggct cggtggtgga tgagcgcggc ttcgtatggg agaaggcggt cgagggcgac    1500
tttttccgcg tgcagtacag cgaaagcaac cacttgcacg tggacctgtg gcccttctac    1560
ccccgcaatg gcgtcatgac caaggacacg tggctggacc accggcagga tgtggagttt    1620
cccgagcact tcctgcagcc gctggtgccc ctgcccttg ccggcttcgt ggcgcaggcg     1680
cctaacaact accgccgctt cctggagctc aagttcgggc ccggggtcat cgagaacccc    1740
cagtacccca accggcact gctgagtctg acgggaagcg gctgaagccc tgataacctc    1800
gcctttgttt ttcgggggtc tgtctggatg tggagaagct ctgtgtgagc ggtgaggggt    1860
ggagggatgt cgcggagagg ggaaggggga aactgaccaa gaaagaaatt ctaaggagag    1920
catgagagaa ggctggcatt ggcaggagga gagcaccagg acgaggatgg gaagcgacct    1980
ccagatttat caaatggtca tgcccactgg gagccgtgga tatgcgtggg gacatcctgg    2040
gtcatctcag tcatggaggg agacggggat gtcacgccgt cccgcagggc ccagcacagc    2100
cccagacccg aaaaaagtgt tctgcccaag attccgagag ccctgcgctc tagggcaggg    2160 gcagagttt ggaaacagtg caggctctgg agccagactg gcgagattca atcctggct      2220 ctatcgcttc ggagccaggt gggcctgggg gggcgtcgca gtctctctgt gcctcagttg    2280
cttccaggat gcgggaccct tggctgcagg ggttgcttcc gccactagag ggcgcgccgg    2340
tcccgctcct ggtggcccac tgtggctgcc cgggcgacag tacgcccagg gcctgtgttc    2400
catagccatc tactctcttg agcctttgga cttctctcca gcccctgtg ggaggcggac     2460 agcagtgacc acctcccctt cttttggact gcgacctcct tccctcctgg gagagccctg    2520
tgacctgcat gctactctta actgttctat tcaagactga atagaagtat ttcagtcttg    2580
cagaggagga aatgctcaga gctccgaggt gcggctgtgg tcgagaaccg ggtgctgggc    2640
cgggcgcggg ggctcacgcc tgtaatccca gcactttggg aggccgaggt gggaggatcg    2700
cttgagccca ggagtctgag accagcctcg gcaacatgcc aagacccgt ctctattttt     2760 aaaaaagaaa aagaaccgac ttctgaatcg cagctccact catgactaat acctcattat    2820
ttcagctgtc tgcacctaat tccccacttg cacggcagtg tagacaataa ccatagctca    2880
cactcactga gcacctactg ggtaccaggc accattctca gtgtttcacc tggatcaact    2940
aatgcgtccc tcacctcagc cctctgaagt gacagctgct attattttca ttacacagat    3000 gaaaagctg aggccagaat cgtgaagtca cttgctcaag gtcaggcagc ttaggaaggg      3060
gcagatcggg ggcttgaacc caggtggtca ggctctggag cccacaattg tcttacccac    3120
```

-continued

```
tatgcccctc tctagtcatg gtccccaaga ggggcttgga gacccactta gcaggtgaaa    3180
gcaatggcag ccttccttat ttgattatgc acctaagaat aaatggtatt tgggcatgta    3240
ttcccaatat gtgtatattt atttataaat atatacagat actattatct gtatgttagt    3300
aataaagctt aaattattcc attttaaaat tatgaatatg aatagggttt tttttatgtt    3360
tcttgcctca tcccaatgac ttttgcacac ccaggtgtga gcacccagca ttcaagacca    3420
cg                                                                  3422
```

<210> SEQ ID NO 7
<211> LENGTH: 495
<212> TYPE: PRT
<213> ORGANISM: Homo sapiens

<400> SEQUENCE: 7

```
Met Arg Leu Thr Arg Cys Gln Ala Ala Leu Ala Ala Ile Thr Leu
1               5                   10                  15

Asn Leu Leu Val Leu Phe Tyr Val Ser Trp Leu Gln His Gln Pro Arg
            20                  25                  30

Asn Ser Arg Ala Arg Gly Pro Arg Ala Ser Ala Ala Gly Pro Arg
        35                  40                  45

Val Thr Val Leu Val Arg Glu Phe Glu Ala Phe Asp Asn Ala Val Pro
    50                  55                  60

Glu Leu Val Asp Ser Phe Leu Gln Gln Asp Pro Ala Gln Pro Val Val
65                  70                  75                  80

Val Ala Ala Asp Thr Leu Pro Tyr Pro Pro Leu Ala Leu Pro Arg Ile
                85                  90                  95

Pro Asn Val Arg Leu Ala Leu Leu Gln Pro Ala Leu Asp Arg Pro Ala
            100                 105                 110

Ala Ala Ser Arg Pro Glu Thr Tyr Val Ala Thr Glu Phe Val Ala Leu
        115                 120                 125

Val Pro Asp Gly Ala Arg Ala Glu Ala Pro Gly Leu Leu Glu Arg Met
    130                 135                 140

Val Glu Ala Leu Arg Ala Gly Ser Ala Arg Leu Val Ala Ala Pro Val
145                 150                 155                 160

Ala Thr Ala Asn Pro Ala Arg Cys Leu Ala Leu Asn Val Ser Leu Arg
                165                 170                 175

Glu Trp Thr Ala Arg Tyr Gly Ala Ala Pro Ala Ala Pro Arg Cys Asp
            180                 185                 190

Ala Leu Asp Gly Asp Ala Val Val Leu Leu Arg Ala Arg Asp Leu Phe
        195                 200                 205

Asn Leu Ser Ala Pro Leu Ala Arg Pro Val Gly Thr Ser Leu Phe Leu
    210                 215                 220

Gln Thr Ala Leu Arg Gly Trp Ala Val Gln Leu Leu Asp Leu Thr Phe
225                 230                 235                 240

Ala Ala Ala Arg Gln Pro Pro Leu Ala Thr Ala His Ala Arg Trp Lys
                245                 250                 255

Ala Glu Arg Glu Gly Arg Ala Arg Ala Ala Leu Leu Arg Ala Leu
            260                 265                 270

Gly Ile Arg Leu Val Ser Trp Glu Gly Arg Leu Glu Trp Phe Gly
        275                 280                 285

Cys Asn Lys Glu Thr Thr Arg Cys Phe Gly Thr Val Val Gly Asp Thr
    290                 295                 300

Pro Ala Tyr Leu Tyr Glu Glu Arg Trp Thr Pro Pro Cys Cys Leu Arg
305                 310                 315                 320
```

```
Ala Leu Arg Glu Thr Ala Arg Tyr Val Val Gly Val Leu Glu Ala Ala
                325                 330                 335

Gly Val Arg Tyr Trp Leu Glu Gly Gly Ser Leu Leu Gly Ala Ala Arg
            340                 345                 350

His Gly Asp Ile Ile Pro Trp Asp Tyr Asp Val Asp Leu Gly Ile Tyr
            355                 360                 365

Leu Glu Asp Val Gly Asn Cys Glu Gln Leu Arg Gly Ala Glu Ala Gly
        370                 375                 380

Ser Val Val Asp Glu Arg Gly Phe Val Trp Glu Lys Ala Val Glu Gly
385                 390                 395                 400

Asp Phe Phe Arg Val Gln Tyr Ser Glu Ser Asn His Leu His Val Asp
                405                 410                 415

Leu Trp Pro Phe Tyr Pro Arg Asn Gly Val Met Thr Lys Asp Thr Trp
                420                 425                 430

Leu Asp His Arg Gln Asp Val Glu Phe Pro Glu His Phe Leu Gln Pro
            435                 440                 445

Leu Val Pro Leu Pro Phe Ala Gly Phe Val Ala Gln Ala Pro Asn Asn
        450                 455                 460

Tyr Arg Arg Phe Leu Glu Leu Lys Phe Gly Pro Gly Val Ile Glu Asn
465                 470                 475                 480

Pro Gln Tyr Pro Asn Pro Ala Leu Leu Ser Leu Thr Gly Ser Gly
                485                 490                 495

<210> SEQ ID NO 8
<211> LENGTH: 35
<212> TYPE: PRT
<213> ORGANISM: Artificial
<220> FEATURE:
<223> OTHER INFORMATION: the signal sequence of murine preprotrypsin,
      His/myc tags

<400> SEQUENCE: 8

Met Ser Ala Leu Leu Ile Leu Ala Leu Val Gly Ala Ala Val Ala Asp
1               5                   10                  15

Tyr Lys His His His His His Glu Gln Lys Leu Ile Ser Glu Glu
            20                  25                  30

Asp Leu Arg
        35
```